United States Patent [19]
Humphrey

[11] Patent Number: 5,157,427
[45] Date of Patent: Oct. 20, 1992

[54] OBJECTIVE REFRACTOR

[75] Inventor: William E. Humphrey, Oakland, Calif.

[73] Assignee: Allergan Humphrey, San Leandro, Calif.

[21] Appl. No.: 510,348

[22] Filed: Apr. 16, 1990

[51] Int. Cl.$^5$ ............................................. A61B 3/10
[52] U.S. Cl. ..................................... 351/205; 351/211
[58] Field of Search ............... 351/205, 206, 211, 212, 351/221, 234

[56] References Cited

U.S. PATENT DOCUMENTS 4,640,596 2/1987 Humphrey .......................... 351/205
4,707,090 11/1987 Humphrey .......................... 351/205

*Primary Examiner*—Paul M. Dzierzynski
*Attorney, Agent, or Firm*—Townsend and Townsend

[57] ABSTRACT

An objective refractor having no moving parts is disclosed. The refractor, which can be either a hand held or table mounted instrument, includes a reference array and an interrogating array projected onto the eye fundus. The reference array is projected from light sources and the interrogating array is projected to light detectors. Both the reference array and the interrogating array are projected onto the fundus of the eye through preselected spaced apart regions of the eye lens. The movement of the reference array with respect to the interrogating array is observed. By the expedient of making at least two sequential observations utilizing at least three separate regions of the eye lens, the amount of relative pattern displacements can be reduced to a requisite optical prescription for the eye.

29 Claims, 15 Drawing Sheets

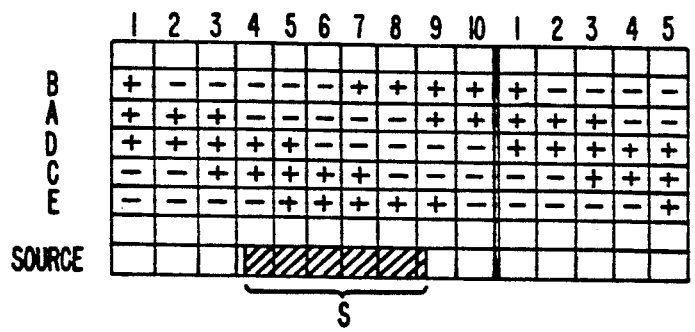
FIG. 9A.
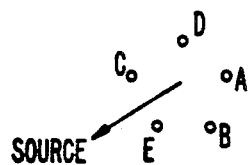
FIG. 9B.
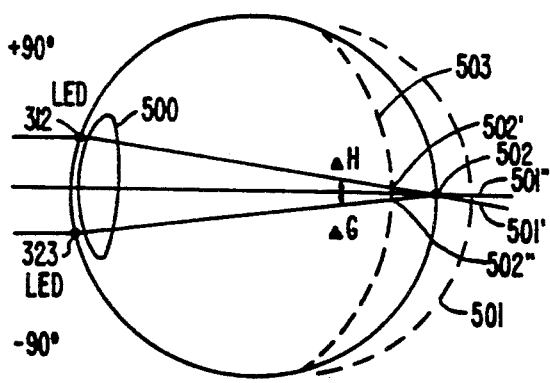
FIG. 10.
FIG. 11A.
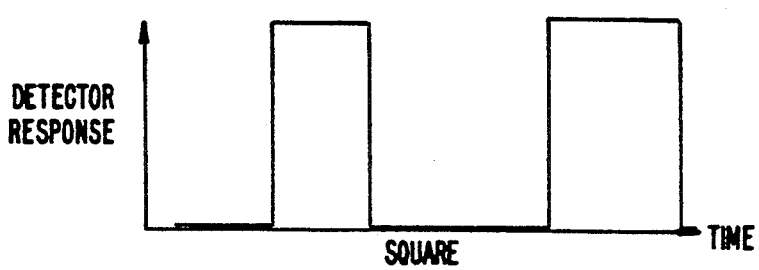
FIG. 11B.

OBJECTIVE REFRACTOR

BACKGROUND OF THE INVENTION

This invention relates to refractors and specifically to an objective refractor having reduced sensitivity to ambient light and improved reliability coupled with lower cost of production.

SUMMARY OF THE PRIOR ART

The cornea of the eye refracts light observed onto a photosensitive image surface, the fundus of the eye. Objective refraction has heretofore consisted of observing from the outside of the eye, image patterns projected to the inside of the eye on the fundus. When these image patterns are optimally recognized, the objective refraction prescription is generated.

Because the fundus of eye is a photosensitive surface, the intensity of light used to interrogate the eye must be at a level where impairment of its photosensitive function does not occur. Consequently it is desired to maintain this interrogating light to a low level or to a spectral band having little photosensitive effect.

Objective refractors have heretofore required relatively moving parts such as lenses placed in the front of the eye for the generation of a corrective eye prescription. These lenses are changed or moved to optimize the view of an image on the fundus of the eye. These lens in front of the eye complicate the objective refraction by adding relatively expensive moving parts and adding refractive interfaces. Very little light incident on the retinal image ever leaves the eye and the addition of refractive interfaces and moving lens members makes the low level light image harder to observe.

In some cases, it is desirable to produce an objective refraction in the presence of intense light sources associated with surgical illumination or diagnostic instruments such as slit lamp systems. These severe ambient light conditions generally render such objective refraction nonoperational.

Accordingly, there is a need for an objective refractor operable with low levels of interrogating light useful in objective refraction of the eye even in the presence of strong ambient light. Further, there is a need to limit relatively moving parts to improve reliability and reduce cost.

SUMMARY OF THE INVENTION

An objective refractor having no relatively moving parts such as lenses for generating corrective prescriptions and a minimum of refractive optical interfaces is disclosed. The refractor, which can be either a hand held or table mounted instrument includes a reference array and an interrogating array projected onto the fundus of the eye. The reference array is the real image at the eye projected from light detectors; the interrogating array is the real image at the eye projected from light sources. Both the reference array and the interrogating array are projected from disclosed patterns where the arrays are interchangeable one with another. Both the reference array and the interrogating array are projected onto the fundus of the eye through spaced apart regions of the eye lens. The movement of the reference array relative to the interrogating array for each region of the eye lens is observed. By the expedient of utilizing at least three separate regions of the eye lens, the amounts of relative pattern displacement can be reduced to a requisite optical prescription of sphere, cylinder and axis for the eye. Preferred patterns of interrogation together with a microprocessor driven embodiment are disclosed.

The preferred interrogating arrays are generated through a "basket weave" or "brick" pattern in which rectangles having a ratio of being twice as long as they are wide are utilized. The rectangles alternate in axial alignment with the major axis and minor axes of adjacent rectangles being alternately disposed at 90° angles. These rectangles with their alternating alignments are separated one from another by a spatial separation of at least one half the minor width of the rectangles. This separation disposes the rectangles in a "basket weave" pattern. This basket weave pattern delimits the boundaries of LED illumination projected through the pattern of rectangles onto the fundus. The interrogating pattern is pupiled at points on the eye lens and expanded to present the interrogating pattern on the fundus.

The LEDs, disposed in an eye lens sampling array are preferably sequentially illuminated. These point sources of light are projected through the basket weave pattern, and have real images of the point sources of light projected to the lens of the eye. The projection of the real images of the LEDs to the eye in effect pupils the light sources at the eye lens on precisely controlled locations. Deflection of the interrogating pattern for each eye lens sample location relative to a reference pattern can be measured to determine prescription. Preferably, the LEDs are duty cycled on the basis of a predicted prescription. Hence each LED effects a sample of the eye lens at precise eye lens locations for each predicted prescription.

The reference array is projected centrally of the eye and overlies the interrogating arrays as the interrogating arrays are projected by each of the LEDs. The reference array is preferably formed out of five discrete aperture types. These five discrete aperture types have their real image projected centrally through the eye in a repeating pattern of the five detectors. The pattern is selected such that the displacement of the interrogating array relative to the reference array can be identified either by the direction of a vector produced from vector addition or alternately the phase of a temporal scan when the interrogating arrays and the reference array are duty cycled, one with respect to the other.

The displacement measurement between interrogating and reference arrays is insensitive to background illumination and consequently provides for rejection of ambient light. Once the deflection of the interrogating arrays relative to the reference array is measured utilizing at least three separate regions of the eye lens, an optical prescription for the eye can be generated in sphere, cylinder and axis.

A microprocessor driven embodiment of the invention is disclosed. The microprocessor accesses in look up table memory values of interrogating LED duty cycles for refractive power in the x meridian, refractive power in the Y direction, and two values of cross cylinder (one for the X direction and one for the Y direction). The eye is electronically interrogated for a peak signal as LED duty cycle entries from each table are sequentially swept through the possible range of prescriptions. Values of power in the X meridian and values of power in the Y meridian are preferably swept first. Maximum signal from both sphere values enable one component of cross cylinder to be computed. Assuming the determined values of sphere, the eye is then swept in the remaining component of cylinder to determine objective prescription. A sequence of rapidly determining patient prescription in a automated mode is disclosed.

Other Objects, Features and Advantages

Because of the relative theoretical complexity of this instrument, the invention will be discretely analyzed. First, the configuration of the optical instrument will be discussed. Secondly, the configuration of the interrogating and referencing patterns will be set forth. The relative movement of these patterns will be disclosed as enabling optical prescription. Finally, and taking the case of one interrogating light emitting diode (LED), the duty cycle of the LED relative to the separate duty cycle of the detectors will be set forth.

Thereafter, I disclose the preferred method relating to the operation of the objective refractor. This method includes supplying a cluster of light emitting diodes, and adjusting the phase of the diodes to emulate the prescription of a patient. Methods for estimating the prescription of the patient, and generating the final prescription of the patient are discussed. A microprocessor driven embodiment is disclosed.

As part of the above disclosure, methods are discussed for eliminating ripple that may be generated by the disclosed phasing of the light sources and detectors. Reference is also made to an accompanying use of light sources in conjunction with a CCD camera to generate prescription, this latter system not now being preferred.

Configuration of the Instrument

An object of this invention is to set forth the configuration of an objective refractor for examining the human eye. The instrument includes an objective lens for producing a conjugate image plane of the fundus of the eye being examined. Interrogating and reference arrays are first projected to the fundus conjugate plane and thereafter relayed to and from the fundus of the eye by the objective lens to determine optical prescription.

The interrogating array comprises an array of light emitting diodes projected through a pattern. Each light emitting diode is focused or pupiled to precise points on an eye lens and thus interrogates different regions of the eye lens being examined. Likewise, the reference array is focused to or pupiled at the central portion of the eye lens being examined. Both the interrogating array and the reference array are relayed between the conjugate image plane of the eye and the fundus of the eye. At this point it should be made clear that although the interrogating array and reference array may be conjugate to the fundus plane for an emmetropic eye, this is not strictly the condition for eyes having other refractive states.

Each LED projects its own separate array of interrogating rectangles. Moreover, the LEDs are each given discrete cycle timing with respect to their position on the eye and the predicted prescription for the eye. These LEDs together produce cumulatively a maximum signal when the selected eye prescription duty cycle timing is appropriate to the actual eye prescription.

The reference array is typically an array of preferably five types of optical elements, each directing light to a corresponding detector element. This reference array is similarly projected to a plane near the conjugate plane of the fundus. Preferably a single reference array is relayed from the fundus conjugate through an aperture which localizes the light rays to a small central region of the eye lens. In this manner, the reference array is relayed to a position of overlap on the various interrogating arrays at the fundus.

The reference array reads the displacement of the interrogating arrays. The detector elements of the reference array are actuated to receive light with each detector element having its own sequential duty cycle with respect to the other detector elements to provide a sequence of interrogation. By establishing proper timing and duty cycle of the LEDs of the interrogating array with respect to the duty cycle of the detectors of the reference array, the prescription of the eye can be determined.

An advantage of the disclosed instrument is that it is capable of being configured in a small package. Consequently, the disclosed instrument can be conveniently "tree" mounted to the instrument pole in an eye examination office or alternatively hand held, or incorporated in a table mounted instrument.

A further advantage of the light emitting diode array is that the size of the pupil can be measured by the device. This pupil size measurement is a useful aside of the instrument herein disclosed.

A further object of the disclosed instrument is that the optical train can be readily altered to that of a keratometer. Accordingly, when the disclosed instrument operates as a keratometer, the objective lens is configured so as to relay the keratometer target images to a common image plane after reflection from the cornea.

A further advantage of the disclosed invention is that the examination of the eye at a matrix of sample points is possible. By the using of a multiplicity of such sample points, the entirety of a fully open pupil can be refracted. While it will be normal to refract the center of the eye lens and ignore the periphery, it should be understood that it is possible to determine the full optical effect of the eye lens, including the periphery, to monitor disease, such as keratoconus of the cornea or to establish the size of regional departures from the nominal refractive state of the eye.

Yet another advantage of this instrument is that the LEDs are duty cycled in their interrogation. Pulsing of the LEDs to short high intensity pulses is possible. Consequently, the LEDs can produce on the fundus light differentials that can be easily detected and seen over ambient light.

Yet another advantage of this invention is that the LEDs can be both cycled in their relative phase with respect to one another and with respect to the detector elements to generate a prescription sensitive signal having significant magnitude over background illumination. At the same time, the LEDs can be duty cycled for high common mode rejection of extraneous signals, especially so-called harmonics.

Configuration of Interrogating and Reference Patterns

A further object of this invention is to describe reference and interrogating patterns. These patterns, when projected to the fundus of the eye, deliver telltale displacement readings of the patterns one to another and enable accurate determination of eye refractive error.

Two distinct patterns are utilized, a reference pattern and an interrogating pattern. Either pattern may be configured to be a light source, and the other is used as a detector pattern for corresponding photosensitive elements. In a preferred embodiment the pattern comprises optical aperture patterns through which are projected light sources onto the eye lens. The reference pattern comprises a second optical aperture pattern which directs light returning from a region of the eye lens onto a set of light detectors. Since the first and second patterns are interchangeable, they will be discussed in this section without regard to the fact that they can be interrogating or detecting in character.

In the preferred embodiment, one pattern has elements in a matrix of two apertures. The pattern of the two apertures are essentially "stackable" or infinitely repeatable into a repeating array. These two apertures from which the large array of any desired size are constructed each comprise rectangles. The rectangle of one aperture has its major axis orthogonally aligned with respect to the rectangle of the other aperture. Half the area of the pattern is made up of these rectangular apertures in the preferred embodiment. The remaining area constitutes a boarder. Each aperture of each rectangle is preferably twice as long as it is wide and has an area that is 5/2nds of the area of elements of the remaining pattern. The rectangles are separated one from another by a boarder having one half the thickness of the minor axes of the rectangles.

Regarding the sensitivity of the so-called brick pattern, either each of the bricks may be provided with discrete sensitivity or the areas of the bricks can be given one sensitivity and the area of the boarders may be provided with a second and different sensitivity. Required sensitivity can be imparted by discrete optoelectric elements, color filters, or preferably by aperture elements capable of deflecting light rays such as arrays of refractive or reflective prisms.

The remaining pattern is composed of five discrete optical aperture types, each preferably with a square configuration. Each of the five aperture types is distinct from the remaining four. Such distinct qualities can be imparted by discrete optoelectric elements, color filters, or preferably by aperture elements capable at deflecting light rays such as an array of reflective or refractive prismatic components.

Each square area is preferably 2/5ths the area of a typical rectangle of the previous pattern. The discrete elements of the five element array are generated in a so-called "knights move" pattern; elements repeat in a "two forward, one to the side" pattern. In fact, the generated displacement pattern represents discrete square roots of a sum of squares equal to the total number of discrete elements used in the reference pattern.

The elements of the reference pattern are selected in such a way that each element of the five elements used has distinctly different neighbors bounding that element on each side. Furthermore, the array of the five apertures are essentially "stackable" or infinitely repeatable into a repeating array of any desired size.

Each element of the five element array when sequentially emphasized, as for example by being sequentially illuminated, causes advancing borders or "fronts" to move across the array. There is a first sequence of emphasis for X-axis sensitivity; there is a second sequence of emphasis for Y axis sensitivity. In the preferred five element array here shown, two sequences of illumination each produce substantially uniform fronts moving through the total array; one front for one sequence moving at right angles to the remaining front for the remaining sequence. It is the detection of these two discrete fronts by their varying degrees of overlap between the reference and interrogation patterns that enables the displacement between the two patterns to be detected.

Relative alignment of the arrays one to another is disclosed. The two element array has the major axis of the rectangle parallel or orthogonal to the progressively moving array fronts. Consequently, overlap of the two arrays results in temporally phased signals or vector directions which are highly sensitive to relatively small movements between the arrays. Consequently, relative motion between the arrays and hence prescription of the eye can be rapidly determined.

An object of this invention is to disclose a sequence of array activation of the preferred five element array. According to this aspect, the array is assigned five arbitrary letter designations, these designations constituting the letters A through E and being illustrated in FIG. 4. A pattern is activated or interrogated in the order AEDBC for sensitivity in one orthogonal direction and in the order ADCEB for sensitivity in the remaining orthogonal direction. (See FIG. 4)

Rules for the expansion of the squares of a matrix are set forth for determining arrays of varying numbers of apertures which are the sum of two squares, this sum not including any number less than five but including 5, 8, 9, 10, 13, 16, etc. A specific example of a matrix having 8 elements is illustrated, it being left to the reader to generate additional matrices in accordance with the teachings of this invention.

An advantage of the patterns is that they are readily interchangeable as either interrogating or reference patterns. For example, I prefer that the five element pattern be the light detecting, reference pattern. However, this pattern can also function as the illuminating or interrogating pattern, the only limitation being that one array illuminate or interrogate and the other detect or form the reference.

A further object of this invention is to disclose two modes of analyzing the relative overlap of the patterns. According to a first embodiment of this invention, one pattern is sequentially illuminated in a timed cycle. In such sequential illumination, the squares of the preferred embodiment are illuminated either singly or in adjacent sets. Responsive to this cyclical illumination, advancing fronts of light sweep across the array pattern in the disclosed orthogonal patterns. These advancing fronts of light having their orthogonal patterns are observed through apertures of the complementary array. Each displaced orthogonal pattern is discretely observed. The resultant phase angle only—and not the magnitude—of produced light modulation contain the requisite displacement information.

According to a second and preferred embodiment of analysis of overlap, the reference and interrogating arrays are duty cycled, one with respect to another, dependent upon the predicted prescription of the patient. The respective observation of overlap between the reference pattern and many interrogating patterns is simultaneously collected, as by prisms deflecting rays from the discrete areas to respective detectors. These respective detectors resolve the light received from the overlapping reference and interrogating patterns in a vector format. The resultant angle (and not the magnitude) of the resultant vector determines the relative pattern displacement.

An advantage of both embodiments of measuring relative pattern movement is that these techniques are not sensitive to amplitude and only sensitive to temporal phase or vector direction. Consequently, the pattern displacement technique assists in rejection of ambient light.

An advantage of this interrogation is that phase or vector determination may be repeated more than once over the expected total deflections encountered for the refraction of the human eye. For example, over a 15 diopter range, three 360° rotations of phase or vector angle might be utilized. There results an expanding scale having greater accuracy.

A further advantage of this aspect is that by assuming spherical and cylindrical aberrations of the eye, it is possible to calculate expected phase angles corresponding to those observed for each interrogating pattern corresponding to various pupil positions. The sphere-cylinder combination which most closely simulates the observed vector phase angles for the various spared apart points in the pupil area represents the preferred refractive finding for the eye.

Yet another advantage of the disclosed technique of pattern overlap is that irregularities on the fundus are in effect averaged over a substantial area of the retina. For example, the structure of the macula lueta of the retina will not appreciably interfere with pattern displacement as its irregularity will be averaged over its surroundings.

A further object of this invention is to disclose a detector configuration that is relatively insensitive to high levels of ambient light. Accordingly, five photosensitive elements in the preferred configuration are each given distinct emphasis by corresponding subsets of directional prisms which make up the interrogating array. The photosensitive elements are synchronous rectifiers, these rectifiers being given polarity and sequence for optimum detection along displacement directions shown in orthogonal axes on the eye.

An advantage of the disclosed synchronous rectifier circuit is that by the expedient of varying the exciting LED duty cycle according to estimated prescription read out, cumulative detector sensitivity results. Assuming 24 interrogating LEDs, a correct prescription will generate 24 times the signal of a random and incorrect interrogation. Over conventional methods, the disclosed timing protocol achieves a sensitivity that utilizing a single interrogating LED would require an increase in sample time in the order of 500 times.

Yet another advantage of the disclosed strength of signal from the detectors is that background lighting is easily discriminated from the phase relation indicating the correct generation of prescription. Consequently, the instrument can be used in high levels of background illumination.

A further advantage of the preferred detector array is that filtering of the received signals to preselect precise frequencies is not required. The disclosed detector resolves vectors from the difference of received signals. The detector is not subject to variations of phase shift in the filters necessary for the resolution of phase in temporal detection formats.

Objective Refractor Operation

Regarding the cycle of the LEDs in their phase relative to one another, the eye is first grossly swept, preferably in sphere, to determine a gross eye prescription. A first sweep is made in meridional power in a first (say x) orthogonal direction; a second sweep in meridional power is made in the second and remaining orthogonal direction. Combining the results of these two sweeps, and resolving one component of cross-cylinder, a best predicted gross prescription is selected.

The LEDs are thereafter given cycle timing relative to the detector array dependent upon their point projection position on the pupil of the eye and the deflection to be expected at that portion of the eye for the gross predicted prescription. This cycle timing is imparted so as to give detectors coupled to the reference array a maximum signal when the prescription is correct. With these cycle timings, it is possible for many interrogating arrays to impact the reference array and its detector with a cumulative signal indicating the determination of the correct prescription. A highly sensitive protocol results which readily signals generation of the correct prescription and incorporates common mode rejection.

A further object of this invention is to disclose a sequence for determining from an estimated prescription the more exact and finally correct prescription. According to this aspect of the invention, the field of LEDs has its interrogating cycle timing shifted by 90° along a field dividing line. LEDs on a first side of the dividing line are shifted by a 90° phase in a first direction; LEDs on a second and opposite side of the dividing line are shifted by a 90° phase in a second direction. Comparison examination of the resulting signal after the phase shifts generates a so-called "discrimination function." This discrimination function indicates both the direction and approximate amount of correction required for determination of a final and correct prescription.

Yet another object of this invention is to disclose an interrogation sequence relative to the respective dividing lines utilized to generate the correct prescription. According to this aspect of the invention, detector array interrogation is made sensitive to displacement between the interrogating array and the detecting array along a first direction. Phase shifting for the determination of the successive merit functions is made as a function of LED position normal to and parallel to the chosen direction of detecting array sensitivity. Thereafter, detector array interrogation is made sensitive to displacement between the interrogating array and the detecting array along a second direction. Phase shifting for the determination of the successive merit functions is again made as a function of LED position normal to and parallel to the second chosen direction of sensitivity. Utilizing the disclosed interrogation sequence, final correct prescription of the eye can be objectively determined.

Regarding the duty cycling of the LEDs, a duty cycle scenario is set forth in which harmonics of significant and interfering proportion are eliminated. Specifically, a duty cycle is disclosed which rejects major contributing harmonics, these harmonics including for the major portion the third and fifth Fourier cosine components.

BRIEF DESCRIPTION OF THE DRAWINGS

FIG. 9A is a temporal plot illustrating the desired polarity of the light sensitive synchronous rectifiers for the signal to be read from a typical LED of a particular phase being illustrated below the temporal plot as a schematic temporal band of lights;

FIG. 9B is a vector plot of the phase of the typical LED as imparted through the synchronous rectifier network of FIG. 9A;

FIG. 10 is an optical schematic of an emmetropic eye with interrogating bands of light focusing at the retina, the figure showing in broken lines a so-called "far sighted" and "near sighted" configuration of the retina for explaining the need to produce phase shifts for interrogation of the eye;

FIG. 11A is a table figure identifying the so-called 5 omega Fourier component;

FIG. 11B is a graphical representation of the source of the so-called 3 omega Fourier component which constitutes a portion of the square wave, it being noted that both the component of FIG. 11A and 11B can be removed by appropriate phase or duty cycle shifting of the interrogating LEDs;

DESCRIPTION OF THE PREFERRED EMBODIMENT

Figure 1:
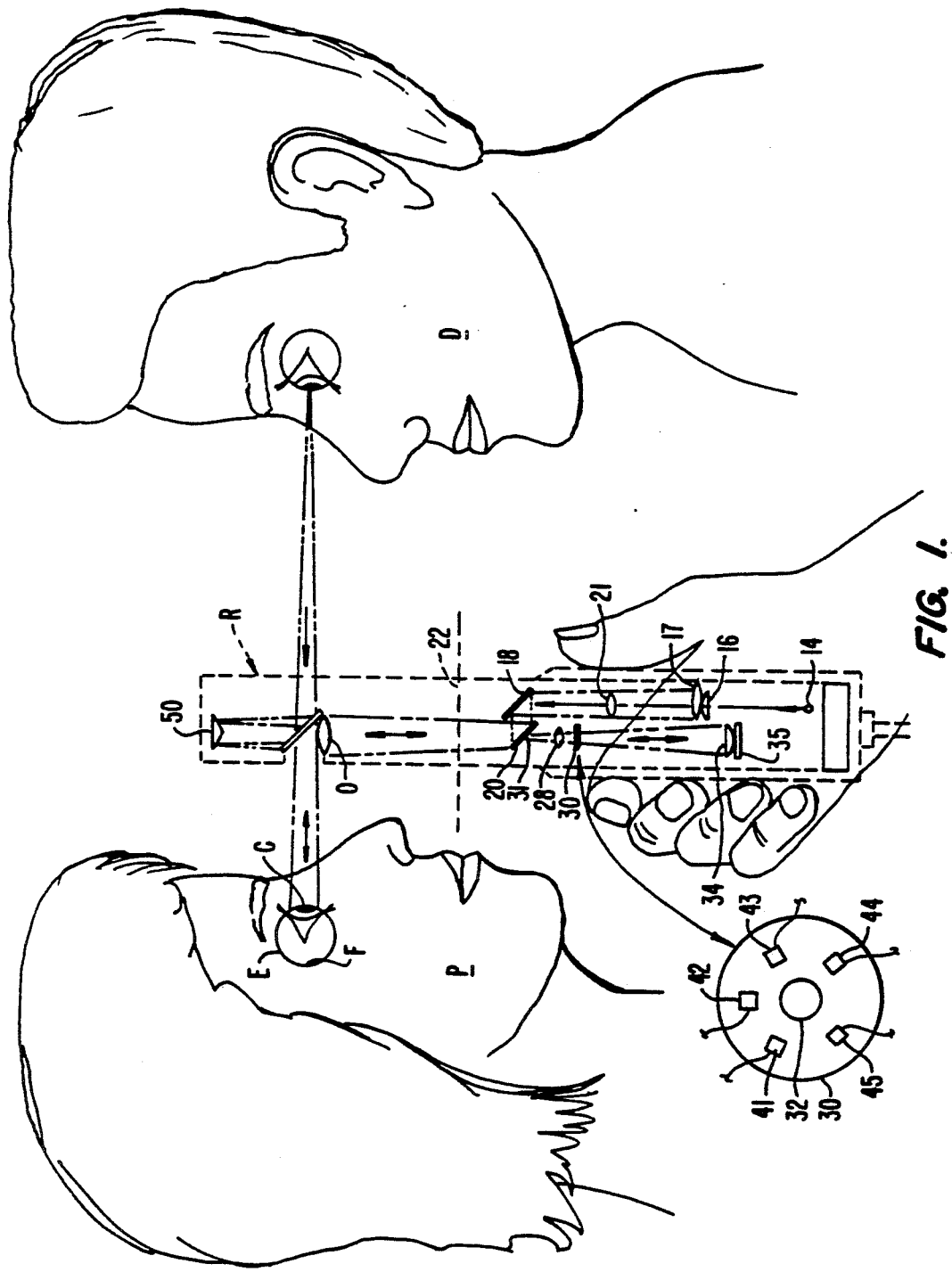
FIG. 1 is a side elevation schematic illustrating an examiner hand holding an instrument objectively refracting the eye of a patient, the instrument here being shown in outline form broken away so that the inner optical paths may be understood and described.

With respect to FIG. 1, a doctor D is shown examining the eye E of a patient P with the hand held objective refractor R. Specifically, interrogating LEDs 14 (only one LED here being shown) project their light through a two element optical brick pattern 16 having the interrogating pattern illustrated in FIG. 3. Light from the LEDs proceeds and is deflected at mirror 18 onto an apertured beam splitter 20. Brick pattern 16 is imaged at a fundus plane conjugate 22 through the action of lens 21. Plane 22 is conjugate through objective lens 0 to the fundus F of eye E. Consequently, an image of optical brick 16 will appear on fundus F of the eye E of patient P. The reader will understand that more than one light source is utilized; consequently, there will be more than one image of the brick pattern on the eye fundus.

Light emitting diodes 14 are projected through lens 17. Lens 17, lens 21 and lens 0 relay an image of the diodes to the cornea C of the patient. Consequently, the image of brick pattern 16 is pupiled at cornea C. This pupil at cornea C enables the light to be incident upon the cornea C at precisely controlled points. Refraction of the light entering through different locations on the cornea causes the brick pattern 16 to appear at corresponding locations on the fundus, depending on the refractive error of the eye.

Having set forth the projection of the image, the receiving path for light returning from the fundus can now be set forth. Specifically, beam splitter 20 has central aperture and a lens 28 which is preferably chosen to relay to the fundus of a normal eye a prism array. As will hereinafter be more fully set forth, the prism array assigns to the discrete detectors the pattern illustrated in FIG. 4.

A detector plate 30 is mounted immediately behind beam splitter 20. Plate 30 includes an aperture 32 through which central rays pass. These central rays are incident at a prism array 34 backed by a mirror 35. (The reader will understand that either the prism array 34 or the mirror 35 may include refractive power.)

The prism array 34 and mirror 35 retroreflect and deflect portions of images from the conjugate plane 22 to the discrete detectors. This image is relayed from the fundus F of eye E of patient P.

The respective images are reflected and deflected to the discrete photodetector array at individual elements 41, 42, 43, 44, 45 on the back side of detector plate 30.

It is the difference in signal received at respective photodetectors 41-45 which enables the displacement of the light pattern to be determined for each interrogating LED.

Figure 16A:
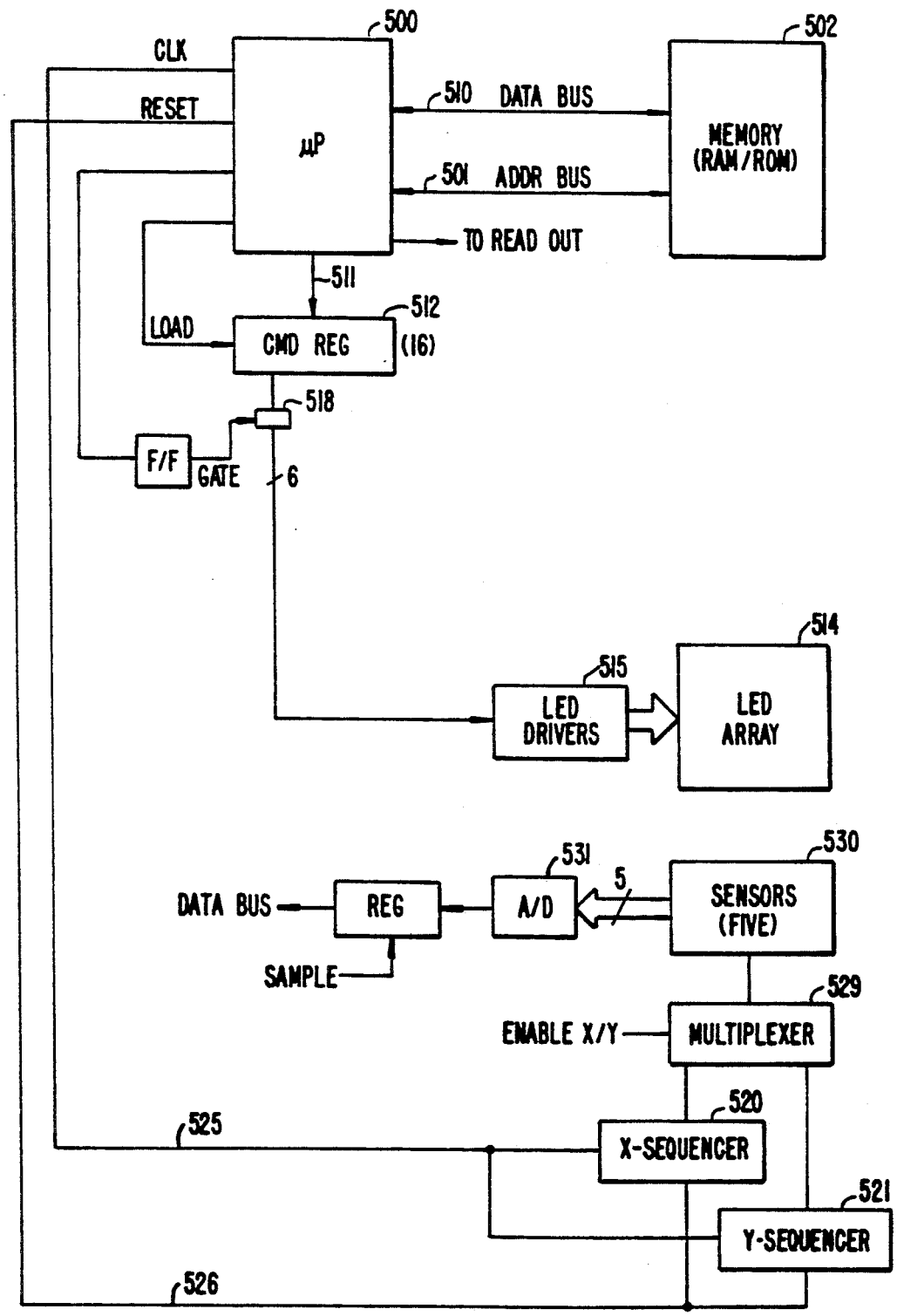
FIG. 16A is a microprocessor schematic illustrating microprocessor hardware for effecting the scanning sequence necessary to generate a prescription with the apparatus of this invention.
Figure 16B:
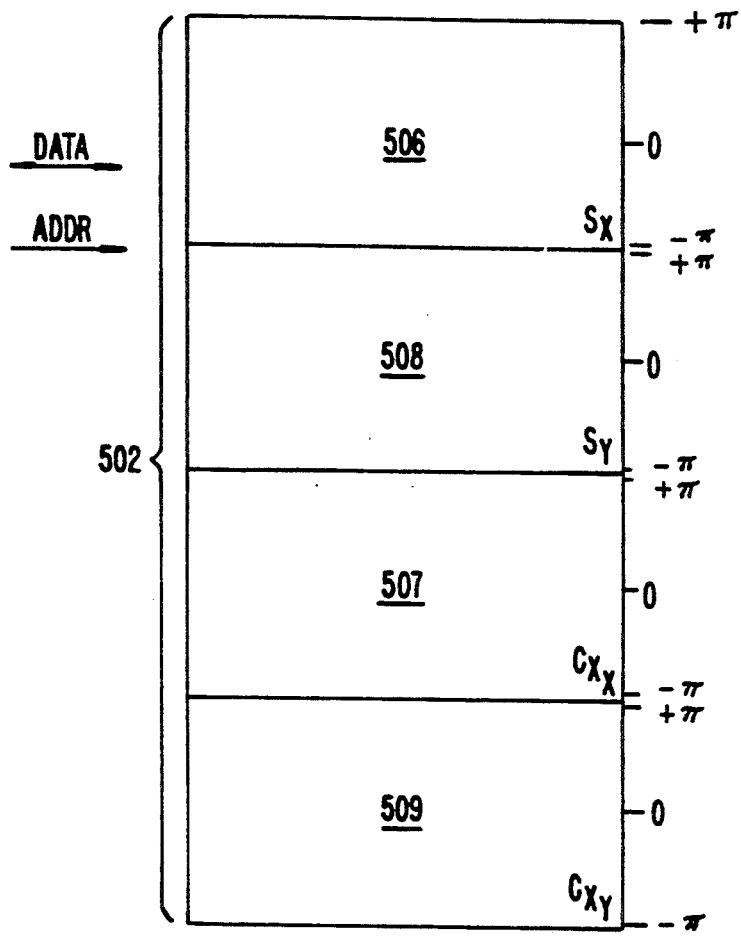
FIG. 16B is a memory schematic for use with the microprocessor of FIG. 16A illustrating of the necessary look-up tables for the determination of a prescription utilizing the apparatus and process herein disclosed; and, FIG. 16C is a schematic of a circuit for effecting illumination of the interrogating LEDs utilized with this invention.
Figure 16C:
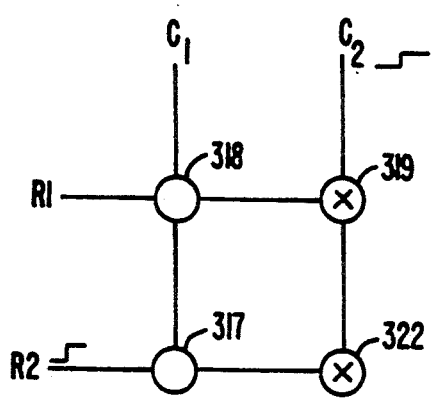

It will be noted that the apparatus is provided with a data display 50 for directly reading out to the eye examiner the observed prescription. This much will be set forth with respect to FIGS. 16A-16C illustrating the microprocessor circuitry utilized with this invention.

Having set forth the preferred instrument, the theory behind the operation of this invention can be further discussed with respect to the schematic illustrated in FIG. 2A-2D.

Figure 2A:
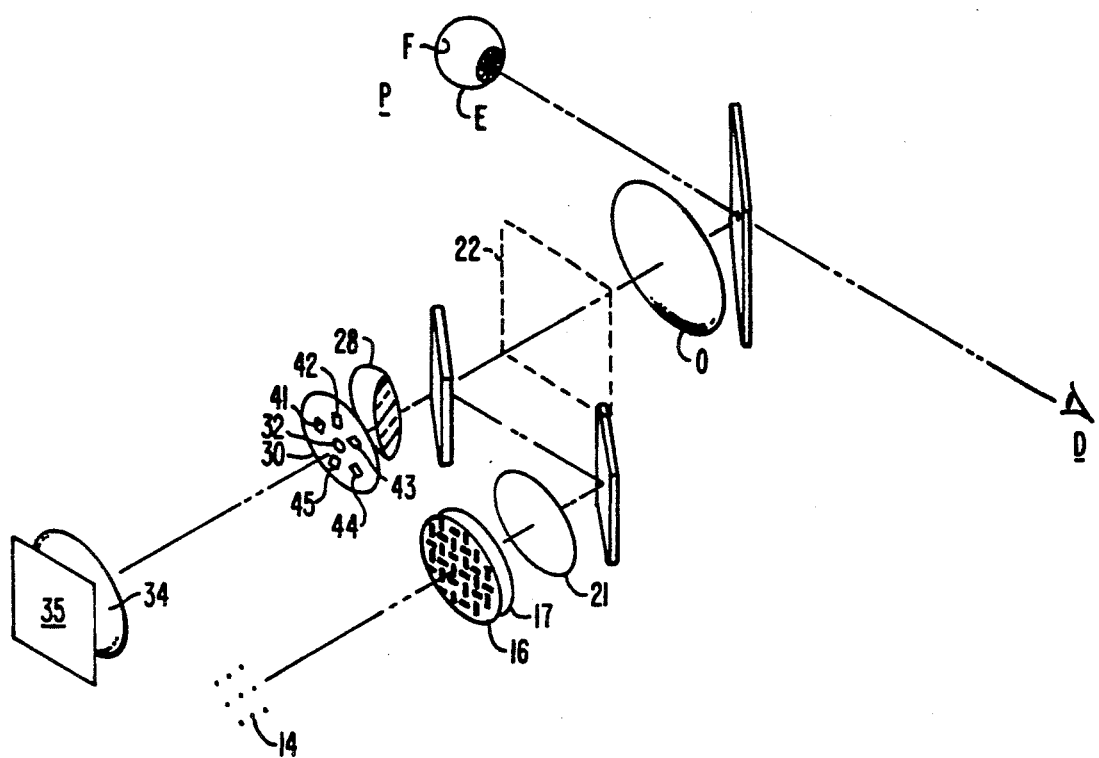
FIG. 2A is an optical schematic of the layout of FIG. 1 utilized for an explanation of FIG. 1.

Referring to FIG. 2A, fundus F from eye E has objective 0 relay an image of the fundus to the conjugate image plane 22. As in FIG. 1, a lens 21 relays a conjugate image of the first array 16 to fundus conjugate 22. Further, a second lens 28 relays a conjugate image of prism array 34 to fundus plane 22. First array 16 is illustrated separately in an expanded view in FIG. 2C. Prism array 34 is likewise illustrated in an expanded view of FIG. 2B. A cornea is illustrated in FIG. 2D.

Prism array 34 is facetted to deflect light to the respective detectors 41, 42, 43, 44 and 45. This array will be more fully set forth with respect to FIG. 2b and FIG. 4.

It will be seen that LEDs include respective array 14. This array can be passed in the entirety through all of the apertures zones of FIG. 3. Array 14 can be passed through the rectangular zones (see I). Alternately, array 14 can be passed through the zones surrounding the rectangular zones. (See II)

The LEDs 14 are in turn relayed to the lens of the eye in pattern 64 by lens 17, 21 and 0. This relay images the LEDs as point sources of light near the plane of the cornea. Thus, the brick pattern 16 is pupiled to point sources of light on the surface of the eye E (see FIG. 2D).

The effect of this pupiling can be readily understood. Specifically, refraction by the eye lens and cornea C will cause light of the array to be deflected. This deflection will be a function of the pupil deflection occurring purely locally at the image points of the LEDs. Thus, the deflection of the rays forming the interrogation pattern will be a function of the local qualities of the lens of the eye at the image point for a particular LED element on the eye lens.

I have shown here the LEDs to be an array of six evenly spaced light emitting diodes, 14A, 14B, 14C, 14D, 14E and 14F. The reader will understand that a greater number of LEDs will be used; it is not possible with the limited space of the drawing of FIG. 2A and FIG. 2D to illustrate such an exemplary spacing. Representative spacings are shown in FIGS. 12A-12D.

Referring both the schematic of FIG. 2A and the expanded view of the eye shown in FIG. 2D, the reader will note that I have not shown an LED registered to the exact center of the cornea C. This reason is that at this exact center location, the reference array 15 is pupiled. This reference array measures the displacement of the various arrays 14A, 14B, 14C, 14D, 14E and 14F. Having a LED project an interrogating array from a light emitting diode through the same aperture as the reference array does not yield useful information as both deflections should theoretically be the same.

Arrays having numerous LEDs have an additional advantage. The total field of such arrays will be obscured at the edges by a partially dilated eye. By having such obscured LED images, the diameter of the pupil, a useful piece of medical information, can be determined responsive to objective refraction in ambient light.

Having set forth the operative portions of the instrument, attention may now be directed to the preferred embodiments of the patterns of elements here utilized.

Figures 3, 4:
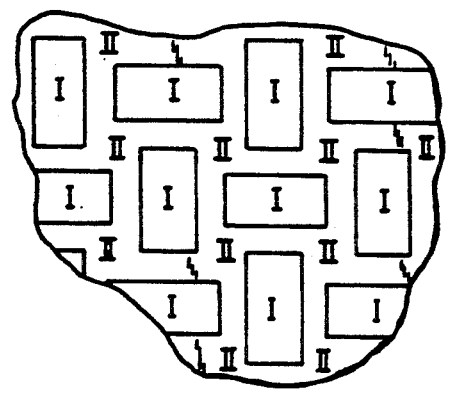
FIG. 3 is a plan view of the interrogating pattern of the preferred embodiment of this invention, this pattern being projected from the pupil represented by each light source image on FIG. 2D to the fundus of the eye.
FIG. 4 is a plan view of the reference pattern of this invention, the illustrated plan view having superimposed thereon directions of displacement labeled "X" and "Y", this pattern being the pattern of detectors that are projected through the central portion of the eye shown in FIG. 2D to the fundus of the eye.

First, and referring to FIGS. 3 and 4, two interchangeable patterns of elements are disclosed. As will hereinafter become more fully apparent, in the preferred embodiment I utilize the pattern of elements shown in FIG. 3 as an interrogating pattern. This pattern of elements constitutes a grid through which the light emitting diodes are pupiled at the lens of the eye. This pattern appears on the retina, deflected from the pupiled position on the cornea responsive to the power of the eye lens.

Referring to FIG. 4, this pattern of elements is preferably used as the reference array. That is to say, it is a pattern of distinct light sensitive areas which serve to define a reference position at the retina of the eye. Each element of the array is made distinct by its own prism facet. Each prism facet—overlying a specific set of areas of the interrogating array at the fundus plane of the eye—causes the returning retinal reflex light to be directed into a set of discrete photodetectors.

The reader should understand that the composite instrument includes one reference array for reading many interrogating arrays corresponding to each interrogating LED.

Figure 2B:
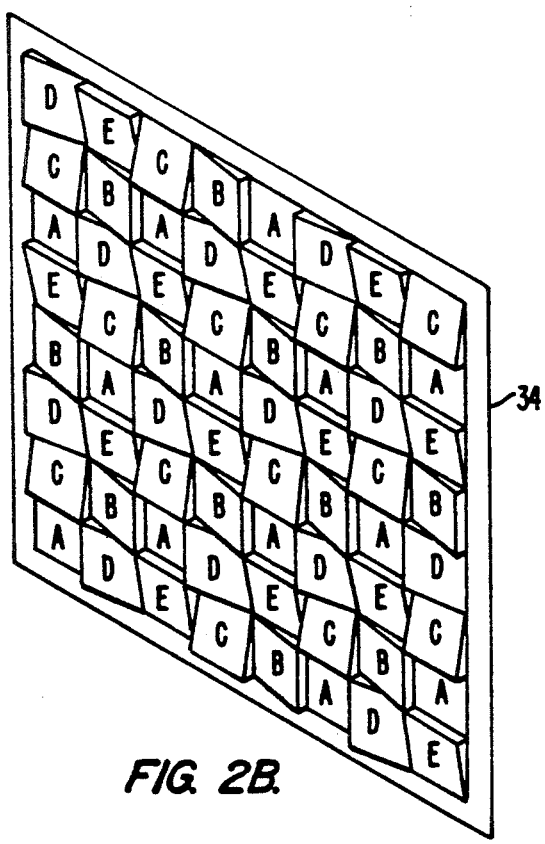
FIG. 2B is an expanded perspective view of five element prism array used in the so-called reference capacity for causing the relay of images from each of the detecting patterns to discrete detectors, this prism array producing the optical pattern that is illustrated in FIG. 4.
Figure 2C:
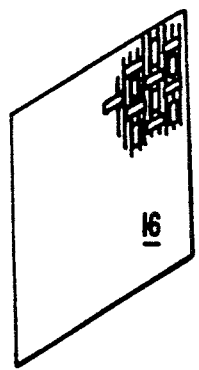
FIG. 2C is a perspective view of the two element interrogating array this two element array producing the optical pattern that is illustrated in FIG. 3.
Figure 2D:
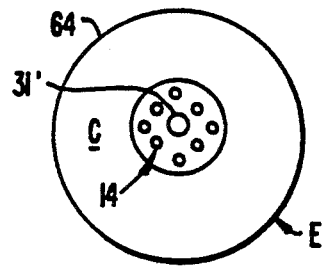
FIG. 2D is perspective view of the cornea of a human eye with the projection of the point sources of the light emitting diodes imaged near the surface of the cornea, it being remembered that the respective patterns of FIGS. 4, 5A and 5B only become visible after the patterns are projected to the fundus of the eye.

Referring to FIG. 2B, a prism array has been illustrated. This prism array has discrete prism facets, labeled respectively A, B, C, D, and E. Prism facets A-E cooperate with the discrete light sensitive elements 41-45. Specifically, each discrete facet is aligned to produce a pattern on the fundus of the eye identical to the pattern illustrated at FIG. 4. That is to say, all of the prism elements A of the prism pattern project an image of detector 41 to the elements A shown in FIG. 4. Likewise, all of the prism elements B of the prism pattern project an image of detector 42 to the elements B shown in FIG. 4. Similarly, all of the prism elements C of the prism pattern project an image of detector 43 to the elements C shown in FIG. 4. Additionally, all of the prism elements D of the prism pattern project an image of detector 44 to the elements D shown in FIG. 4. Finally, all of the prism elements E of the prism pattern project an image of detector 45 to the elements E shown in FIG. 4.

The array of FIG. 4 will appear at two discrete places. First, the array will appear at the fundus conjugate at plane 22. Second, the array will be pupiled at the eye E and thereafter appear on the fundus F of the eye.

It will be understood that the projection of prism elements and the photosensitive elements through the fundus of the eye occurs at a conjugate of aperture 31 relayed to cornea C of eye E. (See FIG. 2D at 31') It is sufficient to say that in appearance at the eye E, the reference array also acts through a small pupiled area—see 31' in FIG. 2D. It is only when the light expands to the pattern of FIG. 4 at the fundus of the eye that the useful expanded pattern of FIG. 4 is ready to interrogate the eye.

Referring to FIG. 4, it will be seen that the areas of the reference array are lettered A, B, C, D, E. Each reference area comprises squares. The elements B, C, D and E are provided with arrows. These arrows here indicate the direction of prism displacement. Element A is without an arrow. This is because in this example, element A passes light through the prism array without appreciable deflection.

Returning to FIG. 3, the rectangles having their major axis disposed vertically or horizontally. In this example, the rectangular areas (I) pass light. The surrounding area is labeled II and does not pass light.

The reader will understand that the following example employs the easier to understand case of the rectangular areas I of FIG. 3 occluding the five element array of FIG. 4. It will be understood that the boarders II about the rectangles could as well be used for the desired occlusion. Further, both of these areas could be utilized, each area being separately utilized from the remaining area.

There is a preferred relationship between the areas of the elements of FIG. 3 and the square areas of the elements of FIG. 4. Specifically, the rectangles are 5/2nds the area of each of the squares. Conversely, each of the squares is 2/5ths the area of the respective rectangles. Further, it will be noticed that each rectangular area is separated from its adjacent rectangular area by an interval equal to one half the width (narrow dimension) of the minor axis of the rectangle.

These dimensions are important. They have been empirically determined with respect to the two element array of FIG. 3 and the five element array of FIG. 4. I have found that this is the combination of arrays having the least respective number of elements. While these particular relative dimensions are important for the array here illustrated, the reader will understand that using techniques similar to those illustrated in FIGS. 5A and 5B, the determination of these dimensions can relatively easily be made once the principles of the illustrated pattern displacement is understood.

Referring to FIG. 3, the elements of the pattern are rectangles and are separated one from another in what appears to be a "basket weave" pattern. Specifically, rectangles with their major axis vertically disposed are centered with respect to the rectangles having their major axis orthogonally and horizontally disposed. The separation between the ends of the vertically disposed rectangles and the sides of the horizontally disposed rectangle is half the width of the minor dimension of the rectangles. Similarly, the separation between the ends of the horizontally disposed rectangles and the sides of the minor dimension vertically disposed rectangle is again half the width of the vertically disposed rectangles. There appears to be a "basket weave" orientation although some prefer the label "brick orientation".

It will be understood that the illustrated dimensions will admit of minor variations. For example, the dimensions of the rectangles of FIG. 3 and the squares of FIG. 4 can be slightly varied. It will be understood however, such variations will detract from the sensitivity for the relative displacements which occur during determining the prescriptive correction for the eye E.

It has been found that the disclosed apertures are ideal for overlay on the apertures of FIG. 4.

Having set forth the simple pattern of FIG. 3, the more complex pattern of FIG. 4 may now be more completely analyzed.

It can be seen that FIG. 4 consists of an array of 5 elements. The elements horizontally are aligned in the order A, D, E, C, B. The elements are each square and hence can form an infinitely repeating pattern if allowed to infinitely extend.

The elements repeat in what might be referred to as a "knight's move" pattern after the well known game of Chess. That is to say, by moving two forward and one to the side, elements repeat.

This repeating pattern is derived from the total number of elements used and a sum of squares which equals this total number of elements used. Here, the total number of different elements used is five: A, B, C, D, and E. The two steps forward constitute the square root of four (4) or a total of two (2). The one step to the side constitutes the square root of 1 or one. It can be seen that the sum of these two squares (i.e., 4+1) is the same as five, the total number of elements used.

FIG. 4 has all "B" elements shaded. These shaded B elements cause a linear front of the elements B to appear. One element front is labeled X, the other perpendicular element front is labeled Y. It is by alignment of the major axes of rectangles I in FIG. 3 to these respective "fronts" that interrogation occurs.

It is with the respective X and Y axes that movement of one array with respect to the other array is described. In the array here shown having five such squares, the lowest number of elements is illustrated which permits unambiguous detection of movement in both the X and Y directions.

Presuming that the X axis advances upwardly and to the right in the Y axis direction, the order of element interrogation can be determined. Starting with the element A, the order is A, C, D, B, E, A, etc. This order can be determined by the reader in observing those elements which an advancing X axis sequentially contacts.

Assuming that the Y axis advances downward and to the right in the X axis direction, the order of interrogation is A, D, E, C, B, A, etc. As will hereinafter be pointed out, by either observing the direction of vectors or alternatively the phase of temporally produced cycles, the relative translation of the elements in both the X and Y directions can be determined.

Observing the diagram of FIG. 4, it will be observed that each square has a four distinctly different element neighbors. Take for example a square B. Nowhere in the disclosed pattern is one square B bounded on any of its four sides by an adjacent square B, or more than one square of the same type.

Further, it can be seen that if the squares are illuminated in the orders specified, advancing wavefronts of light will sweep across the elemental array. Such an order is either A, C, D, B, E (X direction) or A, D, E, C, B (Y direction) or the reverse of either order.

Alignment of the reference array to the interrogating array occurs along the X and Y axis as it is disposed in FIG. 4. The results of such alignment can be best seen in FIG. 5A and FIG. 5B.

Figure 5A:
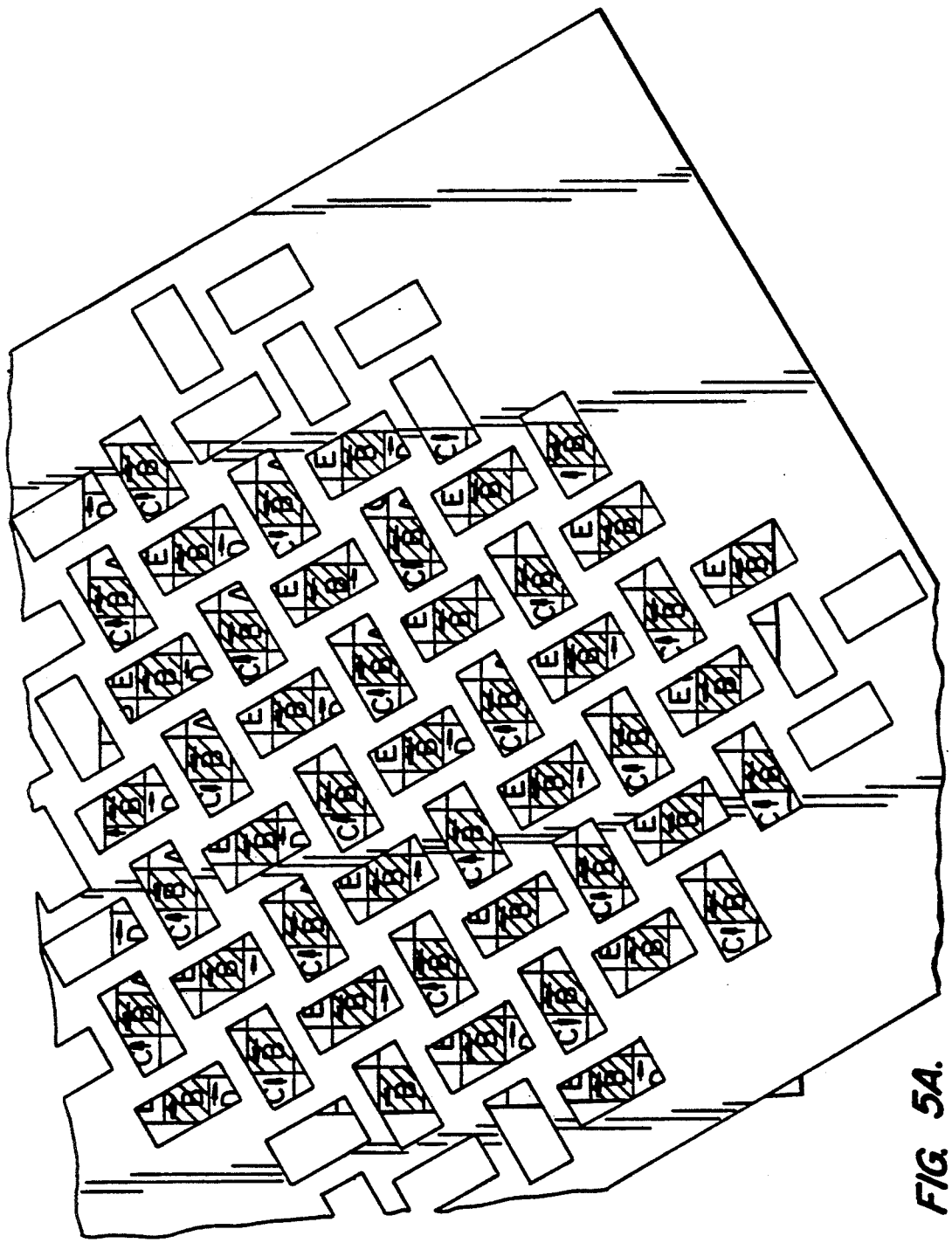
FIG. 5A is an overlay of the interrogating pattern on the reference pattern illustrating the predominance of the "B" elements for the particular displacement illustrated, this pattern being representative of one light emitting diode only.
Figure 5B:
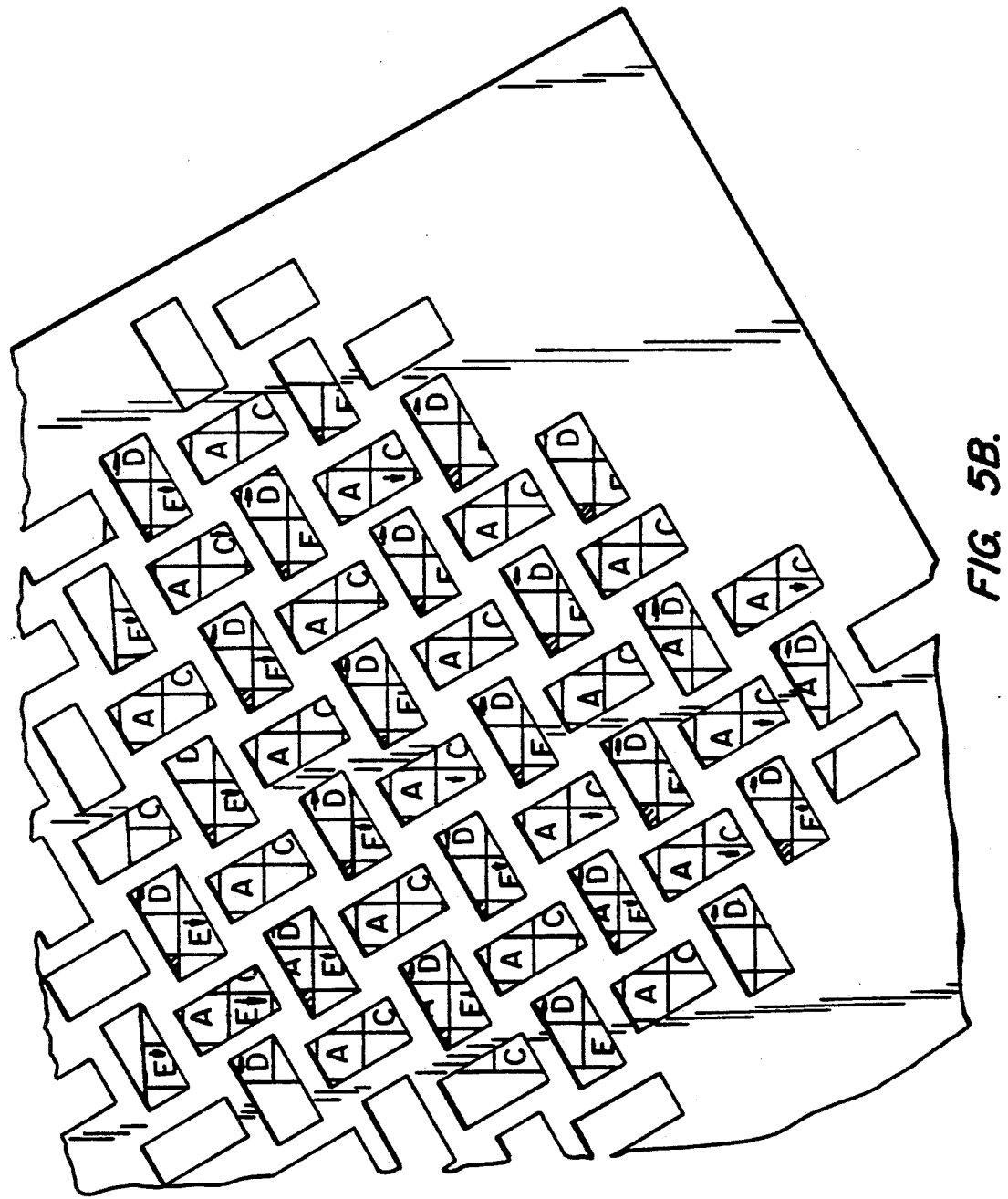
FIG. 5B is an overlay of the interrogating pattern on the reference pattern illustrating the viewing by the patterns of a 180° phase shift from the element "B", this pattern being representative of an alternate light emitting diode but having a differing displacement because of a different point of incidence on the eye of FIG. 2D.

Before analysis of the overlap produced at FIGS. 5A and 5B, at least two important points must be called to the attention of the reader.

First, the functionality here provided is the result of the vector sum of all of the light received from all of the elemental arrays. Only the direction or phase of the sum is important; the disclosed patterns are relatively insensitive to the resultant amplitude.

Secondly, although the examples of FIGS. 5A and 5B illustrate in the case of FIG. 5A, maximum visibility of element B and in the case of FIG. 5B minimum visibility of element B, it is misleading to consider the viewed portion or occluded portion of any single element alone. The device requires for its operation the sum of all elements, the minimum total being 5.

Figure 6:
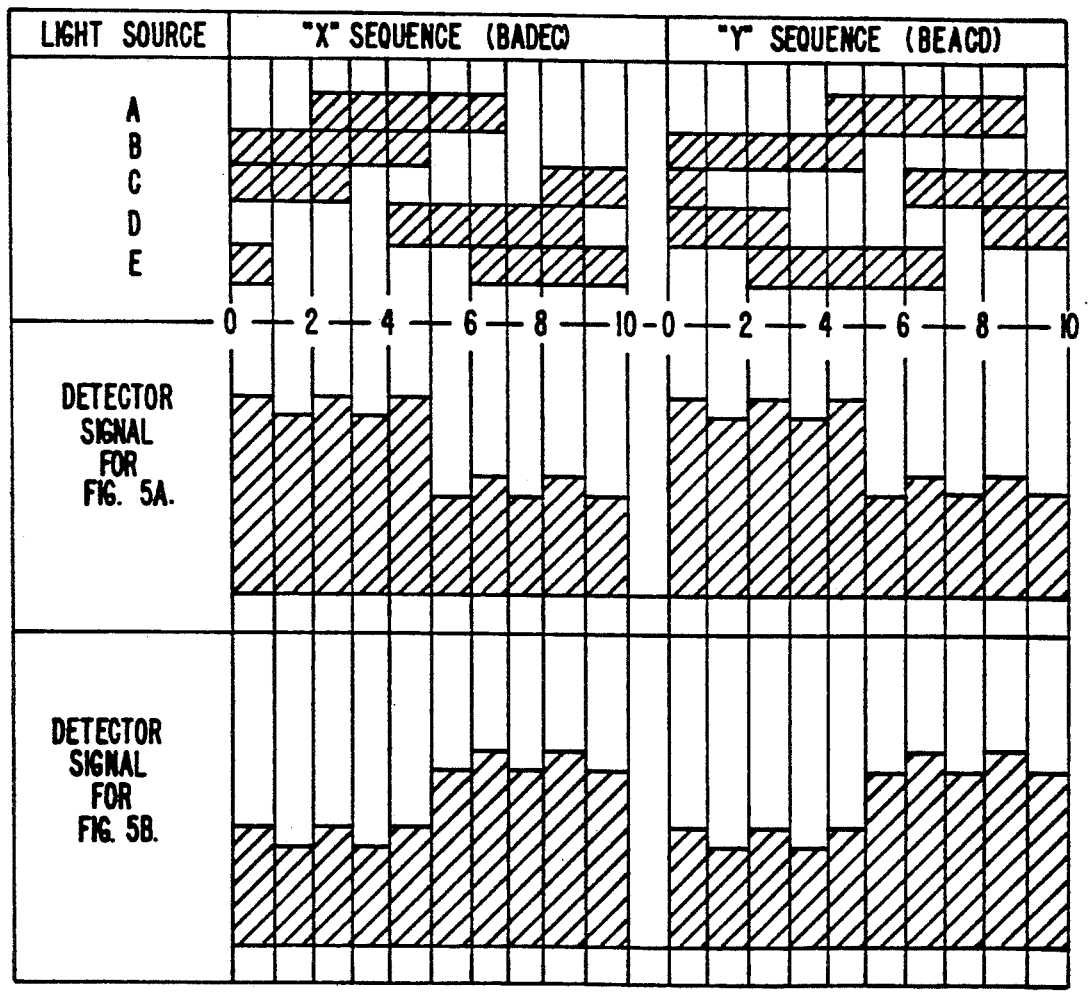
FIG. 6 is a set of temporal plots of the displacements illustrated in FIGS. 5A and 5B.

To assist the reader in further understanding, the plots of FIGS. 6 and 7 are provided. These respective plots assume temporal phasing of the five discrete light sources A-E. The reader will remember that the arrays can be either light sources or detectors. Accordingly, this description will be generically directed to either in the section of this description immediately following.

At this point in the description for ease of understanding of the invention, a 50% duty cycle will be assumed for all light sources, even though this is not preferred Later, the preferred 40% duty cycle will be introduced, it being pointed out that this duty cycle reduces certain harmonic inputs into the resulting output. As the understanding of these harmonic outputs requires understanding of system operation, explanation begins with the 50% duty cycle.

It is previously been mentioned that fronts of light will sweep across the five element display. Such sweeping will occur in either the X and Y direction as indicated on FIG. 4. This will be ACDBE for the advancement of the X axis and ADECB for the advancement of the Y axis. The reader must therefore keep in mind for the following descriptions that sensitivity of the arrays must be discretely activated for the X direction and thereafter discretely activated for the Y direction. Examples of this discrete activation follow.

Turning to FIG. 6, it will be seen that each of the detectors or lights are actuated on a 50% duty cycle. Each cycle has a total of 10 clock counts. Therefore for each detector or light to be on a 50% duty cycle, the device must be on for 5 clock counts and off for the remaining 5 clock counts. This actuation occurs here in the sequence B, A, D, E, C for interrogation in the X direction. The reader will see that with five elements to be evenly timed with respect to one another, each element must be time spaced from other elements by increments of two time counts. (See FIG. 6)

Starting with detectors or lights B, actuation from time period 0 through time period 5 will occur. Detectors or lights A actuate from time period 2 through time period 7, D from time period 4 through time period 9, E from time period 6 through time period 1 and finally C from time period 8 through time period 3.

Referring to FIG. 6, and remembering the displacement directions illustrated in FIG. 4, detector signals for X displacement equal to that shown in FIG. 5A are set forth. Similarly, and with reference to FIG. 5B, detector signals for the same X displacement are set forth immediately below. It can be seen that the two displacements produce two distinctly different temporal images.

The case of Y displacement is also illustrated in FIG. 6. Again commencing with light or detector B and commencing at time period 0, and ending at time period 5, the illumination sequence can likewise be understood. E commences at time period 2 and ends at time period 7. A commences at time period 4 and ceases at time period 9. C commences at time period 6 and ends at time period 1. Finally, D commences at time period 8 and ends at time period 3.

For the displacement given in FIG. 4 in the "Y" direction, a detection pattern for each of the time periods through the pattern illustrated for FIG. 5A is given in FIG. 6. Likewise, the detection is illustrated for the displacement in the "Y" direction in the amount illustrated in FIG. 5B is shown.

It will be understood that reception to or from each of the elements A, B, C, D, E can be indicated in a polar coordinate format. In this polar coordinate format, the respective elements A-E are arrayed circularly in the order of the respective "X" and "Y" displacements. Such a polar coordinate format is set forth with respect to FIG. 7A.

Figure 7A:
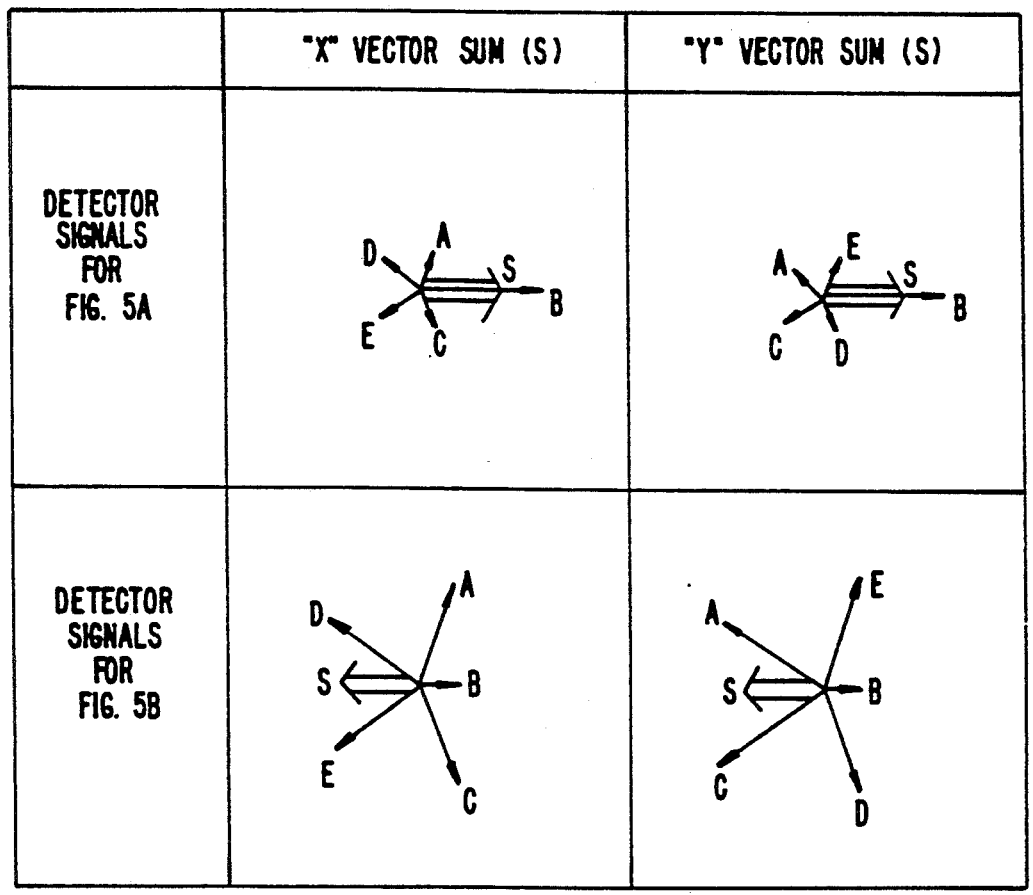
FIG. 7A is a set of vector plots of the displacements illustrated in FIGS. 5A and 5B.

Referring to FIG. 7A and remembering the displacement illustrated in FIG. 5A with the detector signal detected for FIG. 5A in the X direction, a vector diagram has been constructed. In this vector diagram for displacement in the X direction, the vector aligns with B. Similarly, and for displacement in the Y direction, again the vector aligns with B.

As translations gradually occurs from the alignment illustrated in FIG. 5A to the alignment illustrated in FIG. 5B, the vector sum of the elements will rotate. Rotation will occur counterclockwise presuming relative displacement of the pattern in one direction; displacement in the opposite direction will include opposite vector clockwise rotation. In the lower left portion of FIG. 7A, translation has occurred until the vector sum of the discrete elements has been transferred to an intermediate point between the vectors D and E for translation in the "X" direction.

Similarly, in the lower right portion of FIG. 7A, translation has occurred until the vector sum of the discrete elements has been transferred to an intermediate point between the vectors A and C for translation in the "Y" direction. It is to be understood that the vector format for each of the two directions "X" and "Y" is distinct and in the order that each of the elements would be interrogated by translation such as that shown in FIGS. 5A and 5B.

In the 5 position rotational pattern illustrated in FIG. 7A, each of the discrete vectors, D, A, B, E, C, for translation in the X direction and B, E, A, C, D for translation in the Y direction have been illustrated. The vectors have been added to yield a resultant vector direction. It can be seen that the vector direction is produced as the outcome of the respective translation. It is only the vector direction which yields a useful result. Vector magnitude is ignored.

I have previously mentioned that other arrays can possibly be utilized other than the five element array that I preferred. I illustrate such an alternate array in FIG. 7B.

Figure 7B:
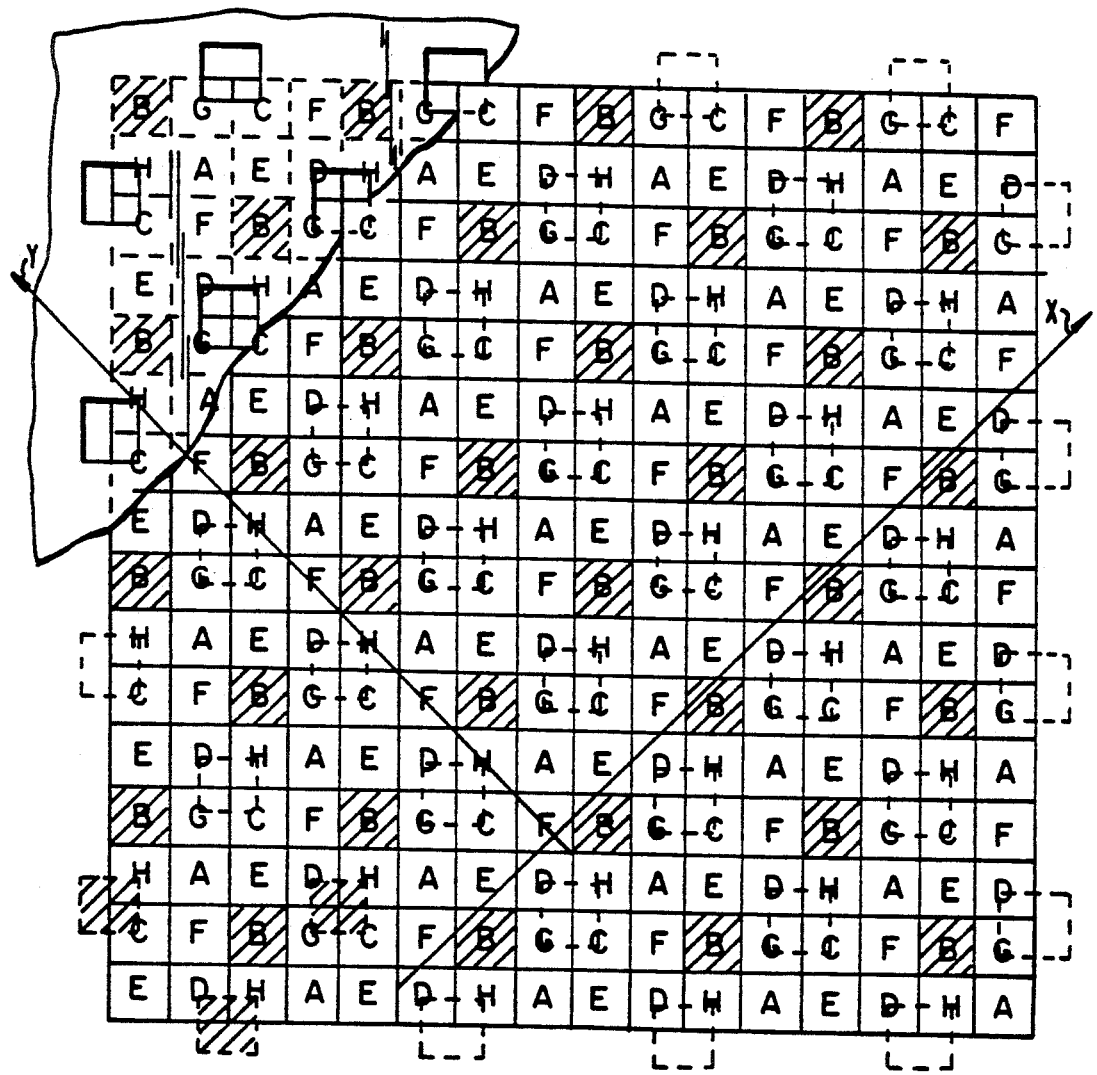
FIG. 7B is an overlay in a manner similar to that illustrated in FIGS. 5A and 5B disclosing the use of an eight element reference array with an overlying interrogating array.

Referring to FIG. 7B, an eight element array is shown. It includes the eight reference elements A, B, C, D, E, F, G, and H. Interrogating elements I are illustrated. The interrogating elements are also squares. These interrogating squares are shown having the same individual areas as the reference squares.

In the embodiment here shown, I have empirically determined that the interrogating squares can be the same size as the squares on the pattern referenced. While other sizes of squares or rectangles can be used, the same size of square here gives a simple output which directly indicates displacement. The reader will likewise understand that the boarders around the interrogating squares could as well be used for interrogation. In this latter case, the interrogating squares themselves would be opaque.

Just as the pattern of squares repeats, so does the interrogating pattern of squares. For example, the interrogating squares I are shown straddling each intersection of the adjacent elements DHGC in the example set forth in FIG. 7B.

The interrogating squares I are shown here straddling the adjacent elements DHGC. This is an exemplary displacement. As further translation occurs, other displacements will be generated.

Referring to the elements ABCDEFGH, these elements repeat in a two forward, two to the side arrayed infinitely stackable pattern. Following the rules set forth with respect to the pattern of FIG. 4, this repeating pattern is derived from a sum of the total number of squares. Here, the total number of elements is eight. The two steps forward constitute the square root of four. The two steps to the side constitute the square root of four. It can be seen that the sum of these two squares is eight, the total number of individual elements used.

All of the elements B are shaded. It can be seen that this shading give two directions of investigation. These directions of investigation are labeled "X" and "Y".

It will be understood that this is the second lowest number of squares that can detect relative displacement between the patterns in both the X and Y directions.

Presuming that interrogation of the advancing wave front parallel to the Y axis in the direction of the X axis is to occur, actuation of detector elements or illuminating elements as the case may be can include sequentially activating elements pairs G—E, C—D, H—F, and A—B (or the reverse of this order).

Likewise, presuming that interrogation of an advancing wave front parallel to the X axis in the direction of the Y axis is to occur, actuation of detector elements or illuminating elements as the case may be can include sequentially activating element pairs E—F, A—C, G—H, and B—D (or the reverse of this order).

The reader will understand that vector and temporal plots can be discretely developed for the illustrated array. By observing the discrete phase of the vector or the phase of the temporal cycles, the relative displacements between the patterns can be precisely determined.

I will hereafter set forth apparatus for the automated observation of the relative displacements between the patterns illustrated in FIGS. 3 and 4. This apparatus will be useful for the five element reference pattern of FIG. 4 and the two element interrogating pattern of FIG. 3. The reader will understand that through simple modification of the disclosed apparatus as to the interrogating pattern projected through element 16 of FIG. 2C and element 34 of FIG. 2B, techniques similar to those disclose hereafter can be used for the generation of a useful result from the pattern of FIG. 7B.

As is similar to the array of FIG. 4, the array of FIG. 7B has been discrete elements with all adjoining elements being distinctly different neighbors. Take any square B for example. Nowhere in the disclosed pattern are the sides of one square B bounded by another square B, or more than one other square of the same type.

Further, it can be seen that if the squares are illuminated in the specified order, advancing wavefronts of light will pass across the elemental array. This order is specified in element pairs immediately above.

The same caveats apply to this array. Directionality and displacement is only supplied by the vector sum of the array. Further, maximum or minimum visibility of any given element is misleading; summation of all elements is required.

It can be seen that the pattern for description of the embodiment herein is precisely equivalent to that pattern used for the disclosure of the five element array. It will be understood that this array is not preferred; it must contain at least three more individual elements than the preferred array of FIGS. 3 and 4.

Regarding the total number of elements utilized in the so-called reference pattern, the reader will recall that I require that the total number of elements used follow a "sum of squares" rule. Utilizing the sum of the squares of one and two, I have developed my preferred five element array illustrated in FIGS. 3, 4, 5A and 5B. Utilizing the sum of the squares of two and two, I have developed the eight element array illustrated in FIGS. 7B. Utilizing the sum of the squares one and three, the reader can develop an array utilizing 10 elements. Other arrays with more numerous elements are all possible. As the arrays increase, so does the difficulty of precisely directing the light sources and detectors to realize the utility of the patterns here disclosed such as FIGS. 4 and 7B.

I therefore prefer to utilize the five element pattern illustrated in FIG. 7A as a detector array.

Figure 8:
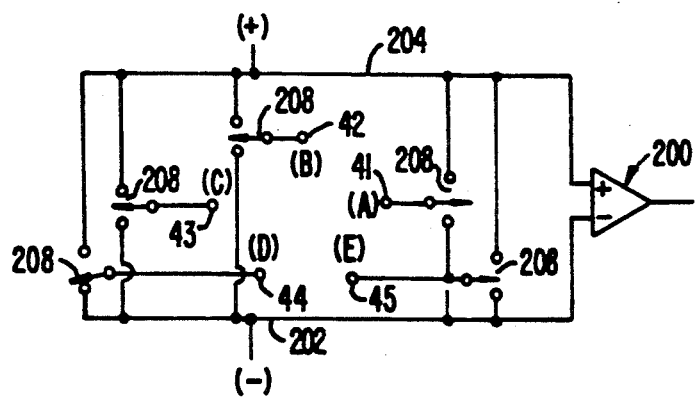
FIG. 8 is an electrical schematic of a detector system for determining the merit function or discriminator function, the detector here illustrated utilizing synchronous light sensitive detectors switched by computer driven analog switches for reading the reference array, the duty cycle of interrogation being taken from the phasing timing diagram of FIG. 5C.

Referring to FIG. 8 the electronics of an appropriate detector scheme for the five element array of my invention is illustrated. In the embodiment of FIG. 8, discrete detectors are switched on and off in a temporal pattern indicated in FIG. 9A. The device utilizes synchronous switches for detecting signals from the various light detectors.

I will hereafter set forth a microprocessor circuit with respect to FIG. 16A. This circuit will disclose the use of two sequencers and a multiplexer to choose between the two for sequencing the synchronous switches for the various light detectors utilized. One sequencer will sequence the switches for sensitivity in the X direction. The other sequencer will sequence the switches for sensitivity in the Y direction. For the present, it will suffice that the reader understand that by using a microprocessor clock signal and paired sequencers, the respective synchronous switches can each be activated to observe the presence of light.

The construction of the circuitry of FIG. 8 is easy to understand. Referring to FIG. 8, a differential amplifier 200 has a negative leg 202 for observing the absence of light and a positive leg 204 for observing the presence of light. Each light detectors A, B, C, D, and E is connected to a respective switch 208. Each of the switches acts under microprocessor controls and switches in a temporal pattern between a positive state and a negative state. The temporal pattern can best be seen with respect to FIG. 9A.

It will be remembered that for purposes of simplicity, we here are utilizing a 50% duty cycle of each of the light detectors 41, 42, 43, 44 and 45. That is to say for half of the respective time period each light detector will look for the presence of light. Signals indicating the presence of light will be output on line 204 and pass through the positive leg of amplifier 200. For the remaining half of the respective time period each light detector will look for the absence of light. Signals indicating the absence of light will be output on line 202 and pass through the negative leg of amplifier 200. Amplifier 200 will emit a signal that is additive of all of the outputs of all of the detectors.

As will hereinafter be set forth, the output of amplifier 200 is important. By the expedient of examining the total intensity of the signal output from amplifier 200, it is possible to ascertain when the apparatus of this invention determines a possible prescription component for a patient being examined.

Referring to FIG. 9A a group of ten time periods is illustrated. It can be seen that the switching here illustrated occurs in the direction of "X" sensitivity. That is to say in the order B, A, D, C, E. Switching for sensitivity in the "Y" direction in the order B, E, A, C, D could likewise occur.

It is required that the respective detectors 41–45 each sample for the presence and the absence of light at evenly spaced intervals throughout the ten (10) period time cycle here illustrated. For the exemplary 50% duty cycle here used, this imparts to each light detector a time period of 5 clock counts where the detector looks for the presence of light and a time period of 5 clock counts where the detector looks for the absence of light. In order for this spreading of the duty cycle to occur over the ten (10) period time cycle here illustrated, it is required that the duty cycle of each detector be offset by two of the time periods from any adjacently cycled detector.

In the example of FIG. 9A, detector B is in the negative state from time period 2 through time period 6; it is in the positive state from time period 7 through time period 1. Detector A is in the negative state from time period 4 through time period 8; it is in the positive state from time period 9 through time period 3.

Detector D is in the negative state from time period 6 through time period 10; it is in the positive state from tim period 1 through time period 5. Detector C is in the negative state from time period 8 through time period 2; it is in the positive state during time period 3 through time period 7. Finally, detector E is in the negative state from time period 10 through time period 4; it is in the positive state from tim period 5 through time period 9.

Assume that a single light emitting diode is given an arbitrary timing. The diode as illustrated in the bottom portion of FIG. 9A switches on at time period 4.3 and switches off at time period 9.2 for an approximate 50% duty cycle. Such a light source timing would be appropriate to an X pattern displacement corresponding to rotation of the vector as illustrated in FIG. 9B.

For example, suppose the relative displacement of a particular LED pupiled to the eye at one location gives the displacement pattern of FIG. 5A. Suppose the relative displacement of a particular LED pupiled to the eye at an adjacent location gives the displacement pattern of FIG. 5B. If the two LEDs are given the same duty cycles, differing detected voltages will emanate from amplifier 200 of FIG. 8 because of the differing overlap between the interrogating patterns and the reference pattern.

Referring to FIGS. 1, 2A, 2B and 2C, it will be remembered that detector element 41 is optically communicated to all the elements A, detector element 42 to optical elements B, detector element 43 to optical element C, detector element 44 to optical elements D and detector element 45 to optical elements E. Such alignments occur by appropriately adjusting the discrete prism facets of the prism array 34 (see FIG. 2B).

I naturally desire to read the individual patterns of my invention with a high signal to noise ratio. I therefore shift the phase of each discrete light emitting diode 14 at each location on the eye E so that for the sensed prescription, each detector element 41–45 receives separately the cumulative light from all of the LEDs. The cumulative reception of light enables my objective refractor to be operable in relatively high levels of background illumination.

Shift of the duty cycles of the LEDs 14 will be set forth hereinafter. Specifically, I will hereafter disclose formulas that can be applied to the specific locations interrogated by the LEDs. These formulas allow anyone having skill in the art to predict the relative displacement between the pattern of FIG. 3 and FIG. 4 for any given prescription of the eye. From these relative predicted duty cycles, the duty cycles of the LEDs 14 interrogating the eye are varied. These variations occur so as to "sweep" the eye for the various prescriptive components in sphere and cylinder. When the eye is swept through a component which is closest to the actual eye prescription, the sequenced detectors 41–45 all receive the strongest possible signal. This strong signal indicates the presence of a prescriptive component in sphere or cylinder that is close to the actual value required for correction of the objective refraction of the eye.

The reader will understand that the prescription of the human eye expressed in terms of sphere, cylinder and axis is complex. Specifically, it is well known that sphere, cylinder and axis are all related one to another utilizing certain well known relationships (formulas) well known in the prior art. I therefore will disclose in summary format a sequence of sweeping the eye—and varying the duty cycle—for the various components of optical prescription. When this sequence is followed, it will be seen that the apparatus and process of this invention is quite capable of making an objective refraction for any normally encountered optical prescription.

Brief reference can be made to the diagram of the emmetropic eye illustrated in FIG. 10. It will be remembered from the description of FIG. 2A that each LED is imaged so a point source of light upon cornea C. Assuming that respective images of LEDs are incident upon the retina of an emmetropic eye at locations 312' and 323', this person enjoying hypothetical "perfect" vision. Assume further that both diodes 312 and 323 are given the time period illustrated in FIG. 9A. Presuming illumination of the "basket weave" pattern of FIG. 3, the patterns of LED 312 and 323 will identically overlap. For example, each of these LEDs may overlap rectangles as shown in FIG. 5B. Since neither LED 312 or LED 323 is relatively deflected upon reaching the retina, both arrays of rectangles will overlap one another.

I have previously illustrated with respect to FIG. 7A the phenomena of the relative displacements of the patterns with respect to one another. Specifically, I have demonstrated that as displacement occurs between the respective patterns, a vector which is the sum of the displacement can be generated. Just as the vector was generated in the case of FIG. 7A for the displacements of FIGS. 5A and 5B, a vector can be generated here for the relative displacement of FIG. 9A. This vector is plotted in FIG. 9B.

It now remains for this pattern of overlap at the eye to be read. This reading must occur through the projection of the images of the detectors 41–45 onto the pattern of the elements A–E shown in FIG. 5B.

Projection of the detector images has been previously set forth. Specifically, detector elements 41–45 will each be projected through prism array 34, with each element being projected in the repetitive pattern illustrated for the elements A–E of FIG. 5A. Presuming that the timing of the illumination of each diode and the timing of the enabling of each detector is the same, the reading of the overlap will be the same for LED 312 and 323.

Now let us presume that the hypothetical eye illustrated in FIG. 10 is hyperopic or "farsighted". Such a condition has been illustrated on the eye of FIG. 10 by shortening the distance between the eye lens and the fundus 503. It can be seen that the central ray of light from LED 312 strikes the upper portion of fundus 503 at point 502'. The central ray of light from LED 323 strikes the lower portion of fundus 503 at point 502".

Remembering that light from each of the LEDs 312 and 323 is projected through the "basket weave" pattern of FIG. 3, it can be seen from the lack of convergence between the two central rays from the respective LEDs that relative displacement will exist between the two patterns. I will suppose for the purpose of the present discussion that the projected "basket weave" pattern of FIG. 5A results from LED 312; similarly I will suppose for the purpose of the present discussion that the projected "basket weave" pattern of FIG. 5B results from LED 323. These differing displacements will result from the refractive power of the eye deflecting the pupiled image of each LED at the eye lens 500 to differing locations 502' and 502" on the fundus 503 of the eye.

Projection of the detector images will be precisely as before. Images of detector elements 41–45 will be projected centrally to the fundus by the prism array in the pattern of elements A–E. This projection will occur through a pupil in the central part of the eye lens and produce the pattern illustrated in FIG. 4. This FIG. 4 pattern will be in the same location on the eye fundus for both illustrated displacements of FIG. 5A and FIG. 5B.

In the above example for the "far sighted" eye, this detector has the characteristic that for an array of light emitting diodes all having the same 50% duty cycle, the detector segments will receive light signals in accordance with FIG. 5A which represents the relative displacement of LED 312 and FIG. 5B which represents the displacement of LED 323.

Let us suppose that the hypothetical eye illustrated in FIG. 10 is myopic or "near sighted". Such a condition has been illustrated on the eye of FIG. 10 by lengthening the distance between the eye lens 500 and the fundus 501. It can be seen that the central ray of light from LED 312 strikes the lower portion of fundus 501 at point 501'. The central ray of light from LED 323 strikes the upper portion of fundus 501 at point 501".

Remembering that each of the LEDs 312 and 323 is projected through the "basket weave" pattern of FIG. 3, it can be seen from the impingement upon the fundus beyond the point of convergence between the two central rays from the respective LEDs that relative displacement will exist between the two patterns, this relative displacement being the opposite of that previously illustrated. I will suppose for the purpose of the present discussion that the projected "basket weave" pattern of FIG. 5B results from LED 312; similarly I will suppose for the purpose of the present discussion that the projected "basket weave" pattern of FIG. 5A results from LED 323. These differing displacements will result from the refractive power of the eye lens deflecting the pupiled image of each LED at the eye lens 500 to the differing locations on fundus 501 of the eye.

The reader will realize that the displacements of FIGS. 5A and 5B illustrate an oversimplification of the various displacements that an eye having other than perfect refractive characteristics will generate. For each individual LED in an array of LEDs, differing displacements will result. Consequently, and in the absence of some adjustment, there will be no predictability at any of the elements 41–45 as to when signal will be received and from what discrete diode signal will be received. Realizing this detection problem, attention will now be devoted to the diagram of FIG. 5C.

Figure 5C:
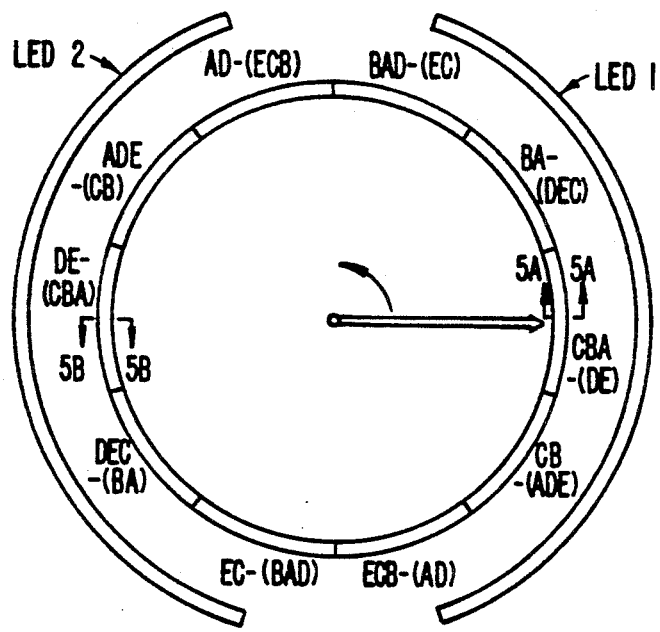
FIG. 5C is a phase timing diagram useful for understanding the sequence of interrogation of the interrogating array of FIG. 3 with the reference array of FIG. 4.

In the review of FIG. 5C, three separate principles will be addressed. First, an order of detector sequencing will be disclosed. This order will be illustrated for movement of the patterns relative to one another in the X direction. The case of the displacement in the Y direction will not be considered completely as it is precisely analogous to the X direction.

Second, the duty cycle of the LED 312 and 323 will be considered. It will be seen that each of the LEDs can be adjusted in duty cycle relative to the displacements of FIGS. 5A and 5B to obtain a maximum signal and a minimum signal. For the purposes of this demonstration, the preferred 40% duty cycle will be used.

Finally, it will be proposed to vary duty cycle of LEDs in an array in accordance with a predicted prescription. Such a variation will be seen to give at the detectors cumulatively the strongest signal. The received signal will be seen to have a highly desirable signal to noise ratio.

Referring to FIG. 5C, a detector timing diagram is shown. The timing diagram includes a circle 600 with ten equally divided arc segments. These arc segments are ordered in the counterclockwise direction.

The vector diagram of FIG. 5C assumes a continuing displacement of the rectangles of FIG. 3 in the X direction of FIG. 4. The displacement occurs from the relative displacements illustrated in FIG. 5A to the relative displacements in FIG. 5B and returning to the displacements of FIG. 5A. In other words, a full "revolution" of displacement is illustrated in the vector diagram of FIG. 5C.

The vector diagram is sequentially labeled. It includes the section 5A—5A for the detection of the displacement of FIG. 5A and section 5B—5B for the detection of the displacement of FIG. 5B. Assuming X axis displacement upwardly and to the right of that illustrated in FIG. 4, counterclockwise vector rotation will result.

For the displacements given, there will be two classes of detector elements. There will be a first class of detector elements illuminated. These are shown at each circle segment representing one tenth of the overall detector duty cycle. At 5A—5A the sequence CBA appears. This means that when displacement of the patterns to the relative position of FIG. 5A occurs, elements C, B, and A are illuminated. Similarly at 5B—5B, the sequence DE appears. This means that when displacement of the patterns to the relative position of FIG. 5B occurs, elements D and E are most likely to be illuminated.

In each position of rotation, some elements are most likely to be vignetted or obscured from illumination. At 5A—5A these elements are elements DE. These elements are shown in brackets (DE). Likewise, at 5B—5B elements CBA are vignetted obscured from illumination. These elements are shown in brackets (CBA).

I have found that it is preferable to actuate the optical segments in the order illustrated by the counterclockwise rotating vector of FIG. 5C. This sequence establishes the desired X axis sensitivity to displacement and enables activation of all communicated light detectors.

It will be remembered that I utilize synchronous light sensitive rectifiers. These elements can be activated in the positive (light receiving) and the negative (nonlight receiving) modes. Accordingly, it will be understood that in any position of vector rotation, all elements 41–45 will be activated—some will be present for the reception of light and will emit signal as light is received; other will be preset for the absence of light and will emit a negative signal when light is received. This much has been previously set forth in the circuitry of FIG. 8.

The next consideration is LED duty cycle timing relative to the established detector cycle. Using the preferred 40% duty cycle, the question becomes for the displacement illustrated in FIG. 5A, what duty cycle illumination of an LED will produce that maximum signal and what LED illumination will produce the minimum signal? These respective LED duty cycles are illustrated. The duty cycle of LED 1 will produce maximum signal; the duty cycle of LED 2 will produce minimum (i.e., negative) signal.

For the displacement illustrated in FIG. 5B, the opposite is true. LED 2 will produce maximum signal and LED 1 will produce minimum signal.

The reader will realize that as the duty cycle of the LEDs is shifted relative to the sequence of interrogation illustrated in the timing diagram of FIG. 5C, signal will decrease. For example, shifting each of the LED duty cycles by one quarter of a full detector cycle will produce an intermediate result in particular, nearly a zero signal.

It will therefore be understood that for each particular displacement along the X direction of FIG. 4 of the pattern of FIG. 3 there will be an LED duty cycle that will result in both a maximum signal being received and another LED cycle that will result in a minimum signal being received.

Realizing that by the shifting of the duty cycle of each of the interrogating LEDs 14 to a duty cycle required by a particular prescription, it will be understood that duty cycles for an array of LEDs can be varied for the determination of prescriptions. As will hereinafter be set forth, these respective various timings for various prescriptions are set forth in a look up table. A microprocessor accesses the look up table. When the correct prescription is interrogated in the look up table, a very strong cumulative signal appears from detectors 41–45. This strong signal enables the correct prescription component to be flagged.

Realizing this much, the case of an LED array can be considered. If an array of LEDs are all given discrete phases which anticipate a predicted prescription, an extremely strong signal will result. The reader will recognize that this "tuning" of the duty cycle is an extremely powerful technique for achieving high signal to noise ratio. By way of example, using an array of 24 LEDs and effecting timing of the LEDs to predict a realized prescription, a signal 24 times that for a single LED will be realized while the detector noise is little changed: more than 500 single LED determinations would be required to achieve this result from 24 cooperating LED sources Having set forth the relative displacement of the patterns upon incidence to the fundus, the use of an entire array of interrogating light sources can now be understood.

Figure 12A:
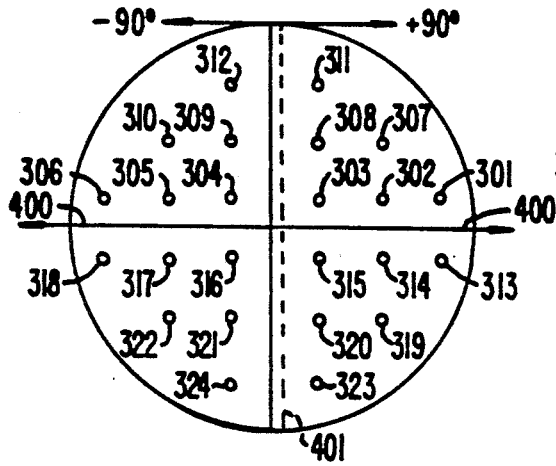
FIG. 12A is a schematic showing an LED field with a vertical dividing line normal to the horizontal direction of displacement sensitivity illustrating the shifting of the phase of the field on either side of the dividing line by opposite increments of 90° to obtain a so-called discriminator function for one component of meridional refractive correction.

First, reference will be made to such an array as illustrated in FIG. 12A. Thereafter, and with reference to the timing diagrams illustrated in FIGS. 9A and 9B, I will set forth how the duty cycle of each interrogating LED can be temporally shifted for given optical conditions of the eye that are not emmetropic. This temporal shift will enable the detector array of FIG. 8 to receive an additive signal from an entire array of LEDs to indicate generation of a correct prescription by the apparatus disclosed herein.

Referring to FIG. 12A an array of 24 light emitting diodes is illustrated. This array includes diodes 301-306, 307-310 and 311-312 on the upper portion of dividing line 400 and light emitting diodes 313-318, 319-322 and 323-324 on the bottom of the dividing line 400.

For a given predicted prescription of sphere and cylinder for each of the light emitting diodes 301-324 a specific displacement can well occur. This displacement will be associated with a temporal shift of the light emitting diode duty cycle which will be shifted to a particular interval of the synchronous sampling of the detector array as illustrated in FIGS. 9A and 9B. It can be seen that assuming the temporal duty cycle of each light emitting diode is individually varied, a maximum sensitivity for the incidence together of all light emitting diodes 301-324 on a detector operating in the temporal pattern of FIG. 9A can be attained. Specifically, and by the expedient of predicting displacement for a suspected prescription and varying the duty cycle as shown in FIG. 9A discretely for each of the 24 light emitting diodes 301-324, all detectors in the array illustrated in FIG. 8 can receive an optimal signal with simultaneity.

I prefer for each prescription component I detect to utilize look-up tables in a microprocessor. These prescriptive components can usually signal the start of the temporal phase of each LED in accordance with suspected prescription.

Thus, by the simple expedient of varying the time period of the 40% duty cycle of each of the light emitting diodes, a reinforced signal simultaneously received from all 24 light emitting diodes can signal correct prescription. It will be understood that the 24 light emitting diodes reinforce one another. In such reinforcement, a signal of unique strength indicating the presence of a correct prescription is attained.

Having set forth the possibility of an LED array being phased for reception of a tuned signal, a digression will be made. Specifically, the digression will refer to FIGS. 14A-14E. A set of equations will be derived to describe standard eye prescription in terms of sphere 0°-90° cross cylinder and 45°-135° cross cylinder. These equations will relate the power of the eye at any particular point to values of sphere and cross cylinder.

Once this determination is made it will be emphasized that to determine sphere, cylinder and axis, measurement of at least three points on the surface of the eye is required. Thereafter, three discrete methods of measuring the power of correction necessary for an eye will be disclosed.

A first method will constitute scanning a group of light emitting diodes with duty cycles anticipating displacement. It will be shown that by scanning in meridional power for both the X and Y directions, sphere and 0°-90° cylinder may be measured.

Second, the use of a charge coupled device will be briefly considered. It will be shown that by using the derived equations, computation of optical prescription is possible. Specifically, by illuminating the eye sequentially through each of the "detector" elements and storing each corresponding video image, computations can be made resulting in the determination of a prescription.

Finally, an additional technique including scanning for error will be disclosed. This technique will be shown to give an indication of error both in sense and magnitude which enables rapid determination of the correct optical prescription.

Figure 14A:
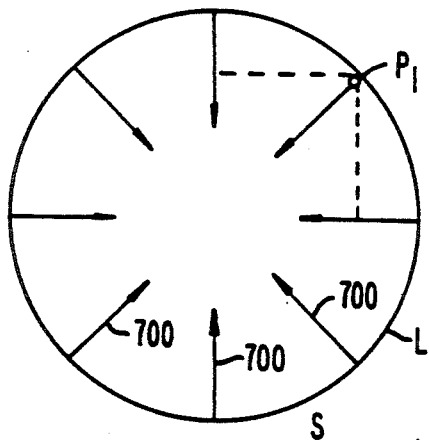
FIG. 14A is a schematic diagram of the eye lens having a positive spherical correction.

Referring to FIG. 14A an optical schematic is disclosed. An eye lens L is shown which lens L is subject to spherical correction. The correction here is positive sphere. This positive sphere is represented by a series of vectors which include a series of inwardly directed radial vectors 700.

Figure 14B:
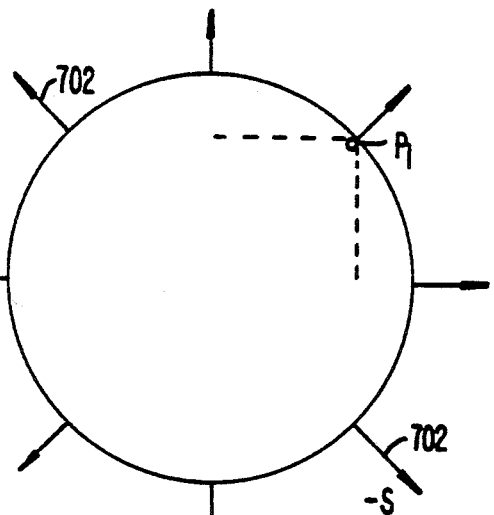
FIG. 14B is a schematic diagram of the eye lens having negative spherical correction.

Referring to FIG. 14B, an eye lens is schematically illustrated having required negative spherical correction. Accordingly a vector format of outwardly directed radial arrows 702 is illustrated for the negative spherical correction.

Figure 14C:
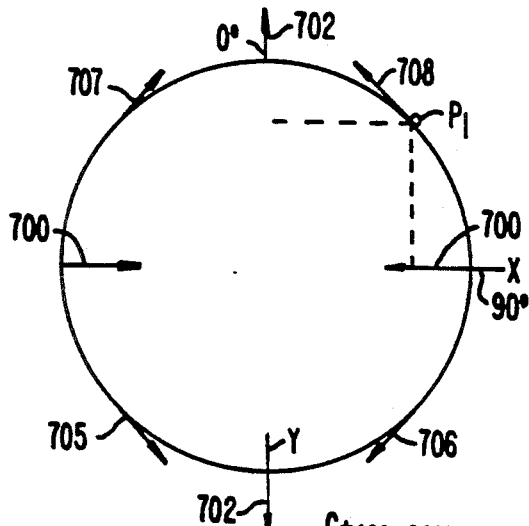
FIG. 14C is a schematic diagram of the eye lens having so-called 0°–90° cylinder.

Referring to FIG. 14C, a cross cylinder is illustrated. The cross cylinder has positive power along the X axis and negative power along the Y axis. Accordingly, it includes inwardly directed spherical vectors 700 aligned to the X axis and negatively directed vectors 702 aligned to the Y axis. Vectors in each of the respective quadrants of the graphical representation are shown. These vectors are a resolution of the vector deflections in the respective quadrants. Accordingly, vectors 705 and 706 respectively resolve the vectors of the respective lower left and lower right quadrants. Similarly vectors 707, 708 respectively resolve the vectors of the respective upper right and upper left quadrants.

Referring to FIG. 14B, a second cross cylinder is shown. This cross cylinder has positive cylindrical power on the 45° axis and negative cylindrical power on the 135° axis. Accordingly, a positive radial vector 700 can be seen on the 45° axis and a negative vector 702 on the 135° axis.

Each of the quadrants are here shown with vector resolution. These quadrants, however, appear on 0°, 90°, 180°, and 270° axis. Specifically, vectors 705′, 706′, 707′, and 708′ resolve the vector powers in each of their respective quadrants of the 45, 135 cross cylinder power here shown.

Figure 14D:
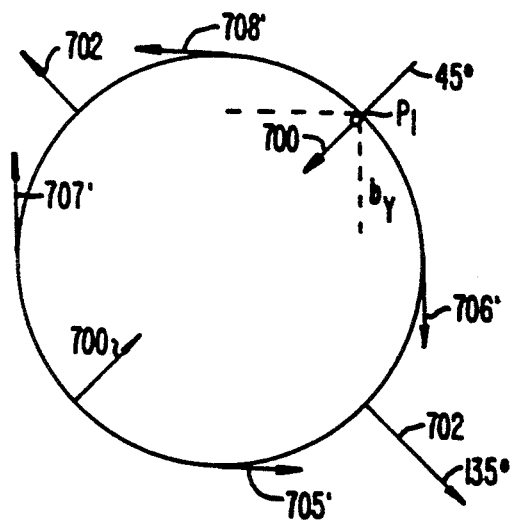
FIG. 14D is a schematic diagram of an eye lens having so-called 45°–135° cylinder; and, FIG. 14E is a schematic of an eye having unknown optical characteristics with the minimum of three points being illustrated on the eye for determination of the traditional measurements of sphere, cylinder and axis with one of the three illustrated points being delineated in X and Y values for determining applicable equations for the computation of sphere, cylinder and axis.

It is known to those skilled in the art that by varying cross cylinder powers as shown in FIGS. 14C and 14D, an overall cylinder of any power and any axis can be generated. I have discussed such a technique in my U.S. Pat. No. 3,822,932 entitled "Optometric Apparatus and Process Having Independent Astigmatic and Spherical Inputs" issued Jul. 9, 1974. Incorporation of that patent is herein made by reference.

I further wish to adopt a convention that will render more clear the terminology which I hereafter adopt. Specifically, for cylinder which is aligned on the 0°-90° axis, I will adopt the symbol $C_+$. For cylinder which is aligned to the 45°-135° axis, I will adopt the symbol $C_x$. It can thus be seen that the C standing for cylinder and the subscript + for 0°-90° and the subscript x for 45°-135° render the disclosed symbols quite understandable.

Figure 14E:
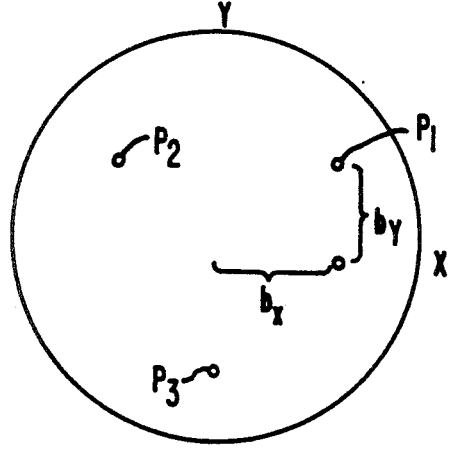

I now turn to the illustration of a hypothetical eye at FIG. 14E. The eye is shown with three respective points, $P_1$, $P_2$, and $P_3$. For a power of sphere, cylinder and axis (or sphere and pair of cross cylinders) to be determined, at least measurement in three such points must occur.

In order to set forth equations by which such a three part solution can be rendered, it is necessary to establish the variables for any given point. Taking the point $P_1$ and referring to the above diagrams 14A-14D can be instructive.

It will be remembered that my measurement technique is sensitive to X direction displacement only and Y direction displacement only. Therefore it is necessary for any point $P_1$ to write an equation which will measure the X axis displacement between the interrogating and reference patterns and the Y axis displacement between the interrogating and reference patterns.

Taking the case of a point $P_1$ and worrying only about the X axis displacement, it can be seen that for the X displacement of $P_i$ the X axis displacement will be generated by any spherical power present such as illustrated in FIG. 14A combined with any $C_+$ power present as illustrated in FIG. 14C. In actual observation, when these two powers combine, they will not be distinguishable. I therefore choose to call these powers meridian power $S_{bx}$ denoting that they are power resulting in pattern displacement in the x direction due to an aperture displacement of "base leg" b.

Referring to FIG. 14D, it can further be seen that as a function of the point $P_1$ in distance above the b axis by a distance $b_y$ another contribution to x axis displacement will occur. This x axis displacement is described by the term $$\left(\frac{C_x}{2}\right)b_y$$

Thus, the equation for displacement in the x axis direction is as follows:

$$\phi_x = S_{bx}b_x + \left(\frac{C_x}{2}\right)b_y \quad [1]$$

Following exactly similar logic the equation for displacement in the Y axis direction due to the location of the point $P_1$ is defined by the equation $$\phi_y = S_{by}b_y + \left(\frac{C_x}{2}\right)b_x \quad [2]$$

I have previously demonstrated that the terms $S_{bx}$ (x axis meridian power) and $S_{by}$ (y axis meridian power) are a combination of sphere and 0°-90° cylinder (see subscript +). The correct equations for these displacements are $$S_{bx} = S + \frac{C_+}{2} \quad [3]$$

$$S_{by} = S - \frac{C_+}{2} \quad [4]$$

Having these equations, three discrete methods of determining prescription for the eye can now be determined.

First, and by the utilization of the foregoing equations, it is a matter for the reader to determine the expected displacement at any of the points $P_1$, $P_2$ or $P_3$. Indeed, I prefer to compute displacement for a matrix of such points. The matrix having the number of light emitting diodes illustrated in FIGS. 12A–12D. It has been found that by varying the temporal relationship of the diode duty cycle with respect to the detector duty cycle (see FIG. 5C) first for x sensitive sequencing and thereafter for y sensitive sequencing, a scanning mode results in a peak signal being determined for the values of $\phi_x$ and $\phi_6$ corresponding to the correct refractive correction. This peak signal plots out with a well defined maxima at the point where meridional power is correctly chosen. Thus, and assuming a first X sensitive sweep for meridional power and a second y sensitive sweep for meridional power, two points of strongest signal will be received.

Figure 15A:
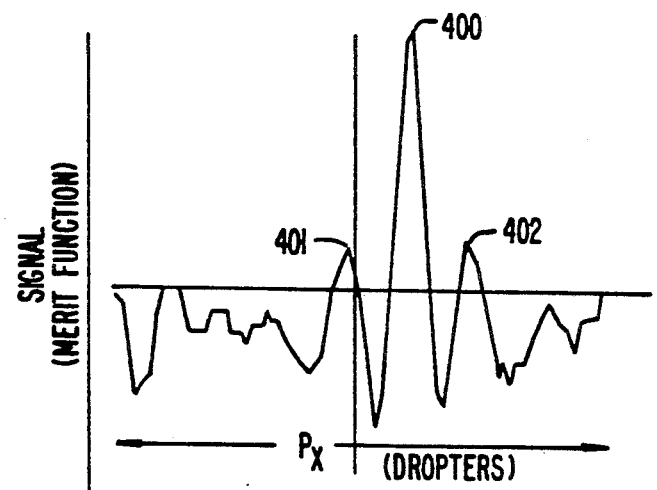
FIG. 15A is a diagram of meridian sphere power plotted against intensity, the diagram illustrating how peaking of the intensity of the received signal occurs when sweep of a value approximating that of the correct prescription along the X axis of eye interrogation occurs.
Figure 15B:
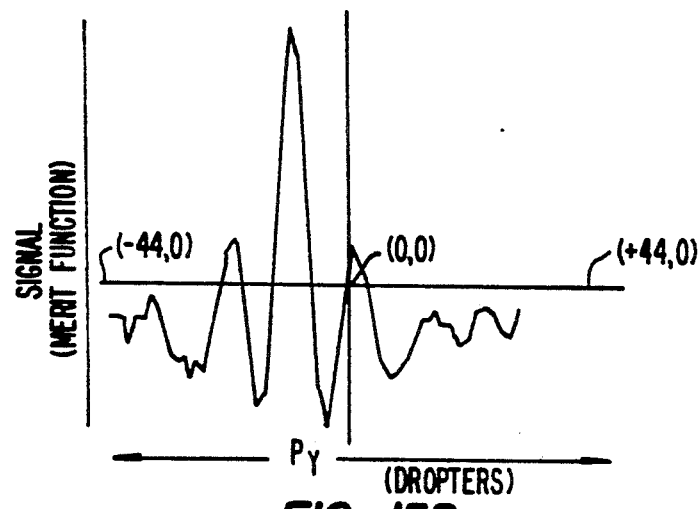
FIG. 15B is a diagram of meridional power plotted against intensity, the diagram illustrating how peaking of the intensity of the received signal occurs when sweep of a different value approximating that of the correct prescription along the Y axis of eye interrogation occurs.

Referring to FIG. 15A I include herewith an actual plot of signal produced by scanning in so-called meridian power. The meridian power was varied by varying the duty cycle of light emitting diodes. The diodes were varied to emulate a spherical prescription ranging from +44 dropters to −44 dropters.

Observing FIG. 15A, it can be seen that there is present a peak 400. This peak coincides to that portion of the scan that is closest to the required correction for a patient. Adjacent peaks 401 and 402 may also be observed. These respective adjacent peaks are false maxima. It is because of these false maxima I prefer to conduct (at least initially) a full scan of the possible ranges of sphere and cylinder. This full scan prevents the apparatus from determining a prescriptive component has been reached at peaks 401, 402.

It can be seen that the graph of FIG. 15A is obtained by having the detectors interrogate the respective pattern of FIG. 4 using the X direction sensitivity. It will be remembered that X direction sensitivity is obtained by scanning the photosensitive elements 41–45 as communicated through the prism element 34 of FIG. 2B to the pattern of FIG. 4 in the order A, C, D. B, E, A, etc.

As similar graph is obtained for Y direction sensitivity, it will be remembered that Y direction sensitivity is obtained by scanning the photosensitive elements 41–45 as communicated through the prism element 34 of FIG. 2B to the pattern of FIG. 4 in the order A, D, E. C, B, A, etc.

We now make the assumption that there is no cross cylinder $C_x$. It can be seen from equations 3 and 4 above that if the curves are coincident, the term for 0°–90° cylinder $C_+$ will be 0. If the maxima of the spherical sweep curves are separated one from another by a distance, it has been found that distance is an approximation to the cylinder component $C_+$.

Figure 15C:
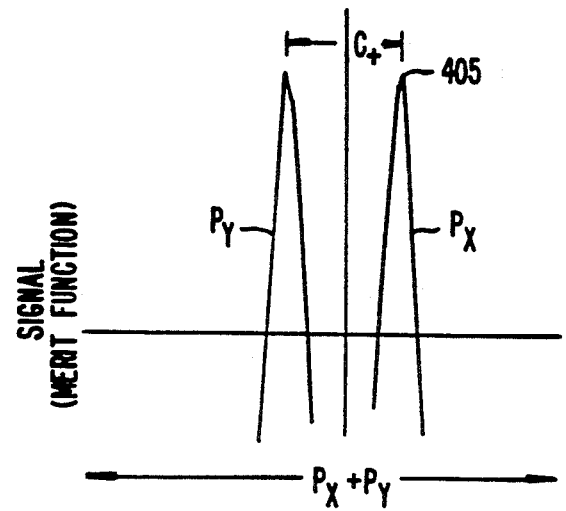
FIG. 15C is a diagram of the peaks illustrated in FIGS. 15A and 15B plotted on the same axis for meridional power with the difference in the peaks plotting as a 0°-90° cross cylinder (presuming instrument alignment with the horizontal and vertical)

Referring to FIG. 15C, I illustrate a plot having the intensity of the X interrogation plotted with respect to the intensity of the Y interrogation. It can be seen that two peaks appear; one peak 405 appears for the X direction interrogation and one peak 406 appears for the Y direction interrogation. It further can be seen that these respective peaks are separated one from another by a distance. This distance has been found to be magnitude directly proportional to the value of 0°-90° cylinder $C_+$.

It may be further seen that using equations [4] and [5] we may determine a value for sphere. At this juncture, values will be known for sphere S, and for the 0°-90° cylinder $C_+$. By the simple expedient of maintaining the two known maxima for Sx and Sy, a sweep for so-called 45°-135° cylinder can be made. Specifically, one sweep for Cx will be made for the X direction of interrogation and one scan for Cx will be made for the Y direction of interrogation. When the maximum function is found, very close estimates for sphere S, and cylinders $C_+$ and $C_x$ will be present. By the simple expedient of iteration, the true prescription may be generated.

With respect to FIG. 16A, a microprocessor embodiment of this invention is disclosed. In this microprocessor embodiment I disclose the use of four look up tables for scanning the eye to determine eye prescription. These look up tables are set forth with respect to FIG. 16B and include spherical power in the X direction, spherical power in the Y direction. Cx in the X direction and Cx in the Y direction. From the foregoing explanation, the reader will understand that these look up tables will be all that is required to determine the prescriptive power of the eye in sphere S and cross cylinder C+ and Cx.

The reader can understand that the disclosed computations could as well be made by a charged coupled device (CCD) receiving the images from the eye. Specifically, in such a protocol, each discrete light emitting diode would be cycled in turn. The CCD would view the intensity variations in the pupil plane resulting from retinal pattern taking each element of the CCD image as an aperture at the pupil of the eye, the image intensities for a series of 5 image exposures provides sufficient information to define the phases $\phi_x$ and $\phi_y$ displacements from each diode. The CCD element position and its estimated values for $\phi_x$ and $\phi_y$ allow equations 1-4 will be solved. The solution, a function of numeric processing, will yield the correct sphere, cylinder and axis for the eye.

I at present do not prefer the use of the charge coupled device to the assignment of the discrete duty cycles to the LEDs. This being the case, I include the foregoing summary only for completeness of the disclosure and to note that the use of a charge coupled device is possible.

I further have made it clear that an array of light emitting diodes is preferred. Such an array can be patterned after those arrays illustrated in FIGS. 12A through 12B. In such arrays 24 light emitting diodes are utilized. These diodes are labeled 301-324. The reader will understand that in a look up table, the discrete timing of the duty cycles for all of the LEDs can be set forth for the full range of each of the prescription components to be scanned.

Having set forth the usefulness of using 24 discrete light emitting diodes, all with varying timing to give unique reinforcing signals in both X and Y sensitive modes, two useful characteristics of the disclosed displacement interrogation will be set forth.

First, and with respect to FIGS. 11A and 11B, the problem of harmonics will be addressed. Thereafter, and with attention first to FIG. 10 and thereafter to the diagrams of FIGS. 12A-12D an interrogating sequence will be set forth.

Referring to FIG. 11A, a "ripple" effect of the utilization of five time periods is illustrated. In FIG. 11A, it is presumed that each of the detectors B, A, D, C, E has a 50% positive duty cycle and a 50% negative duty cycle. As before, these respective duty cycles are averaged over a time period of 10 units for half or 5 of the ten units of time. The detectors are in the positive state half the time. For the remaining 50% of the 100% duty cycle, the synchronous rectifiers are in the negative state.

As before, the temporal phasing of the detectors is illustrated for sensitivity in the X direction. Displacement is one time unit out of a total of 10 time units between the leading edge of the successive sensitivity of each of the detector units B, A, D, C, and E. Here detector B is negative for time period 2 through time period and positive from time period 7 through time period 1. The sequence continues with respective two unit displacements for the detector sequence B, A, D, C, E.

Assuming that a light source is given a 50% duty cycle and is illuminated from time period 2 through time period 6 for five discrete units, addition of the state of each of the total of five detectors is instructive. Specifically, during time period 2 one excessive negative state will be present. During time period 3 one excessive positive state will be present. During time period 4 one excessive negative state will be present. During time period 5 one excessive positive state will be present and finally at time period 6 one excessive negative state will be present.

For the entire time periods 2 through 6, it can be seen that this is a total of three negative states and two positive states. Thus, the negative states will for the light source illustrated at 404 predominate by one negative state. (See FIG. 11A)

Assume an elemental shift of the time period and illumination of a light source in a 50% duty cycle commencing at time period 3 and ending at time period 7, it can be seen that there will be an excessive positive state by the addition process just illustrated. The negative state of time period 2 will be eliminated. The positive state of time period 7 will be added. Positive states from time periods 3, 5, 7 will exceed by one negative states from time periods 4 and 6.

Referring to the lower portion of FIG. 11A it can be seen that as displacement occurs, oscillation will occur from a negative state to a positive state at a frequency of approximately five times the total time required for one-half of a complete detector cycle.

I have dubbed this phenomena a "five omega ripple"; two solutions suggest themselves.

First, by the simple expedient of adapting a 40% duty cycle, this ripple can be eliminated. This is preferred and is illustrated in FIG. 5C.

Second, successive duty cycles of each LED can be displaced by 1/20th of a cycle. Displacement in one direction (for example forward in time) by 1/20th of a cycle followed by displacement in an opposite direction (for example, retardation in time) by 1/20th of a cycle in the opposite direction will eliminate this "five omega" ripple phenomena when the results are combined.

Referring to FIG. 11B, an additional ripple phenomena is therein illustrated. Referring to FIG. 11B, I have discovered that a second so-called "three omega ripple" is present. Simply stated, the Fourier series includes a harmonic contributor of three omega. Again, two solutions are present. The first solution is to alter successive interrogating time periods by 1/12th, commencing one lighting state at a positive 1/12th time period and the remaining state at a negative 1/12th time period.

I have discovered that a timing count which is a multiple of 2, 3, and 5 is to be preferred. For example, instead of using the normal binary count of 256 I prefer to utilize a timing count of 240. Taking a 40% duty cycle, it can be seen that 96 counts comprise precisely 40% of a 240 time period cycle. Likewise by advancing or retarding an illuminating diode in the order of 20 of the total of 240 time units, the "three omega" ripple phenomena just discussed can likewise be eliminated.

An additional method of generating eye prescription once the gross prescription is estimated involves dividing the field of interrogating light emitting diodes into sectors, the sectors can be shifted in phase to produce an error function or discriminator function. This error function can be understood by first utilizing and understanding the diagrams of FIGS. 12A through 12D.

Referring to FIG. 12A, an array of 24 LEDs 301-324 is set forth. These LEDs include LEDs 301-312 above a horizontal dividing line 400 and LEDs 313-324 below horizontal dividing line 400. The reader will remember that by setting the discrete timing of each of the LEDs 301-324, a vector signal of relatively great magnitude over the background illumination would be simultaneously received at each of the individual detectors A-E in the array of FIG. 8.

Two phenomena rise from the division concept illustrated in FIGS. 12A-12D. It will be first demonstrated that assuming optimum signal has been received and the prescription detected by the instrument is correct, by shifting the phase on one side of the dividing line 400 by plus 90° and simultaneously shifting the phase on the opposite side of the dividing line 400 by $-90°$, the signal at the detector apparatus of FIG. 8 will disappear for original phases appropriate to the refractive error.

Second, and assuming the same kind of phase shift but further assuming that the prescription is not correct, a vector function which I call a "discrimination" function will be generated. This "discrimination" function will have a magnitude and sign indicating the required sense and approximate magnitude required for correction of an estimated prescription to a correct prescription.

Referring to FIGS. 9A, 9B and 12A, and assuming the emmetropic eye of FIG. 10 at fundus 501, the reader will remember that there is no relative displacement from the vector configuration of FIG. 9B for each of the LEDs 301-324. That is to say, all of the LEDs can be timed to give the vector addition seen in FIG. 9B, which vector will have relatively great strength over ambient background illumination.

It will be seen with respect to FIG. 12A, sensitivity is in the "X" direction. It can further be seen that phase dividing line 401 for the phase shift is normal to the direction of shift sensitivity.

Now assume that LEDs 301, 302, 303, 307, 308, 311, 313, 314, 315, 319, 320, 323 are each shifted positively 90° in phase. Assume that the remaining LEDs are each shifted negatively 90° in phase. As these groups of LEDs are on opposite sides of the dividing line 401, the equal and opposite shift in phase in the amount of 90° will cause the detector array of FIG. 8 to go from a maximum signal to no signal at all for either of the two groups of LEDs. A zero signal will indicate by its null signal that the test prescription of the moment is correct. If the estimated retractive error was incorrect, the signal will be non-zero, and increase in strength in proportion to the size of the misestimate.

I have assumed in the description generated thus far that the meridional component measured by the light array divided on dividing line 401 and phase shifted in opposite 90° components to left and right of dividing line 401 was correct for the prescription being measured. It is a surprising result of my invention that if the component is other than correct, by the phase shifting process described with respect to FIG. 12A, a signal indicating the component error will originate. This signal will indicate in both sign and magnitude the sense and magnitude required for correction of the particular component being measured.

It will be understood that the phase shifting process of FIG. 12A must be repeated for each of the suspected components being tested. Specifically, and for each component of prescription measured, shifting will occur on opposite sides of a dividing line to opposite 90° phase differentials.

Figure 12B:
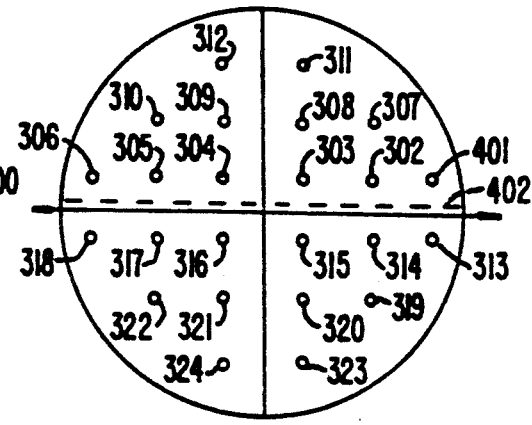
FIG. 12B is a schematic showing the LED field of FIG. 12A with a horizontal dividing line parallel to the direction of displacement sensitivity illustrating the shifting of the phase of the field on either side of the dividing line by opposite increments of 90° to obtain a so-called discriminator function for the 45-135 so-called "oblique" component of eye correction.

Shifting as indicated in FIG. 12B along a dividing line 402 parallel to the direction of X sensitivity will give a sensitivity to 45°-135° components—useful in the determination of astigmatism.

Figure 12C:
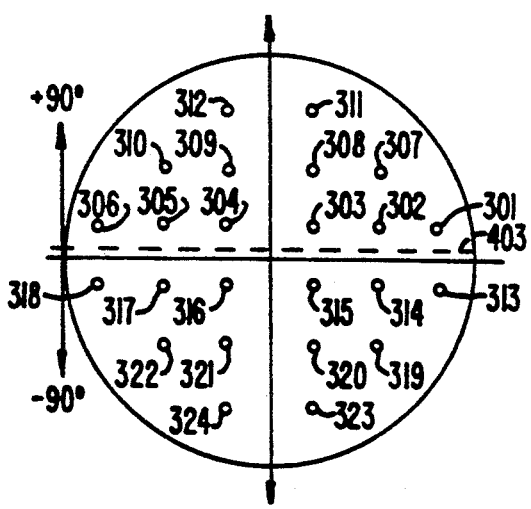
FIG. 12C is a schematic showing the LED field of FIG. 12A with horizontal dividing line normal to the vertical direction of displacement sensitivity illustrating the shifting of the phase of the field on either side of the dividing line by opposite increments of 90° to obtain the second and final component of meridional power correction, it being noted that the scans illustrated in FIGS. 12A, 12B and 12C are sufficient in their total for the generation of a prescription.

Shifting as indicated in FIG. 12C along a dividing line 403 normal to the direction of Y shift sensitivity will give the second and remaining meridional component of prescription.

Figure 12D:
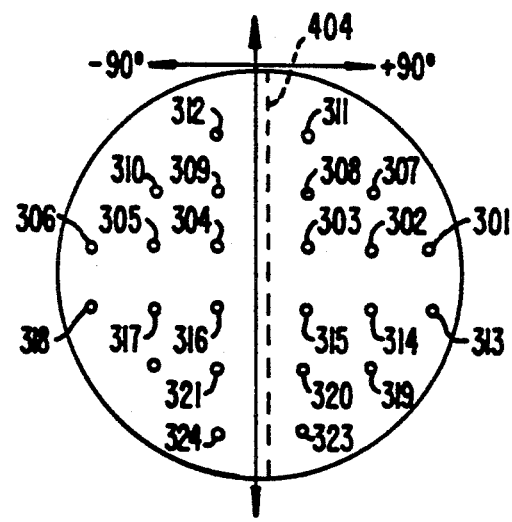
FIG. 12D is a schematic similar to FIG. 12B showing the LED field of FIG. 11C with a vertical dividing line parallel to the direction of displacement sensitivity illustrating the shifting of the phase of the field on either side of the dividing line by opposite increments of 90° to obtain a so-called merit function for the 45°–135° so-called "oblique" component of eye correction, the information obtained being redundant to the information obtained in FIG. 12B; and, FIG. 13 is a schematic of the objective refractor of this invention with attachments for keratometry attached so that the instrument has both objective refraction capabilities and keratometry capabilities.

Finally, shifting as indicated in FIG. 12D along dividing line 404 parallel to the direction of Y shift sensitivity will give a second and redundant 45°-135° component of sensitivity.

In each case, should an error be present in the particular component being detected, a signal indicating both the sense and magnitude of the required correction will be generated. By the expedient of applying this vector indicated correction to the next iteration for the indicated component of prescription, the total prescription for the eye can be rapidly generated.

Figure 13:
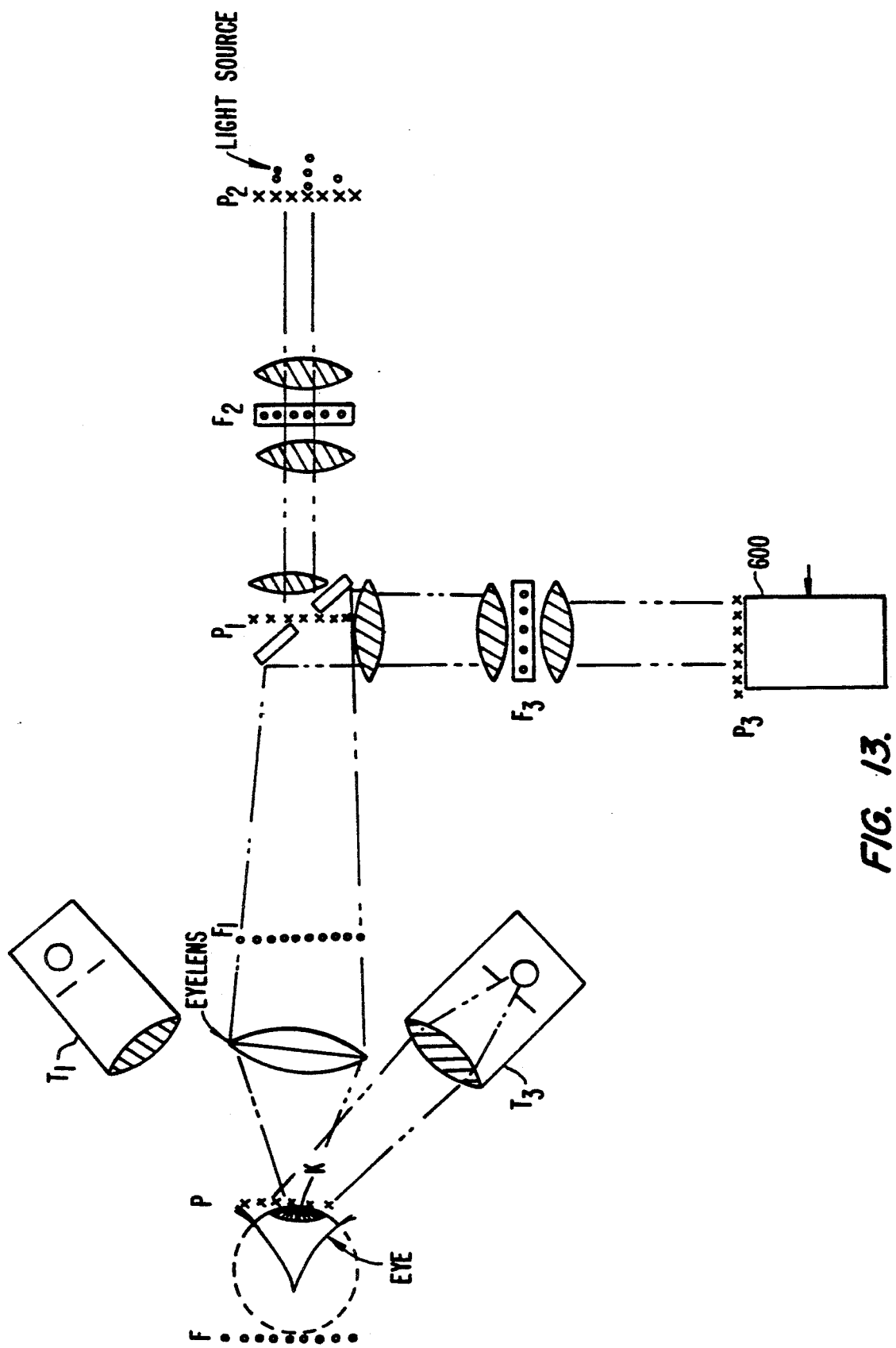

Referring to FIG. 13, it can be seen that the optical arrangement of the instrument particularly lends itself to the addition of targets T useful in keratometry. Referring to FIG. 13, two targets T1 and T3 of four preferred keratometry targets T1 through T4 are illustrated. These keratometry targets are measured in their apparent separation in reflection from the patient's cornea K by a video imaging device such as charge coupled device 600. By the expedient of having the charged coupled device read out the apparent separation of the targets T1-T4, the curvature of the cornea K in sphere, cylinder and axis can be readily determined.

Referring to FIG. 16A, a microprocessor embodiment of this invention is disclosed. The microprocessor includes three main operative functions for the practice of this invention. These functions are a look up table for communicating to the LED array the various duty cycles for sweeping the eye in prescription. Secondly, two sequencers which control two multiplexers. These respective multiplexers initiate interrogation in the X direction and the Y direction by the respective photosensitive elements. Finally, the microprocessor recognizes the various signal peaks when they are encountered. From the recognition of the signal peaks, eye prescription in sphere and cylinder can be computed.

Regarding the duty cycle communicated to each of the light emitting diodes, microprocessor 500 addresses through address bus 501 a look up table 502. Look up table 502 is divided into four sections, these sections having been previously described with respect to the preferred protocol for locating the prescription of the eye. These sections of the look up table are schematically illustrated in FIG. 16B.

Referring to FIG. 16B, it can be seen that a first portion of the look up table 506 includes information corresponding to values of sphere dependent upon variations of LED position with respect to X displacement. These values are computed using the relationships of equation [1].

A second portion 507 of the look up table includes information corresponding to values of Cx for displacement in the X direction. These values will be computed utilizing the relationships of equation [1].

A third portion 508 of the look up table includes information corresponding to values of sphere dependent upon variations of the LED position with respect to Y displacement. These values can be computed utilizing the relationships of equation [2].

Finally, a fourth portion 509 of the look up table includes information corresponding to values of cross cylinder Cx with respect to variations of the LED position with respect to Y displacement. These values can be computed utilizing the relationship of equation [2].

Each of the tables preferably contains information corresponding to ranges of sphere and cylinder which encompass the vast majority of possible refractive errors likely to be encountered.

Having set forth the layout of the look up table 502, the sequence of examination can now be set forth. For the determination of prescription, the eye will typically be swept in one component of sphere power. This component of sphere power can include Sx for meridional power sensitivity related to displacement in the X direction.

Typically microprocessor 500 will address memory 502 at portion 506 on a block by block basis, each block corresponding to a value of sphere. I will assume that a full duty cycle will comprise a count of 240. For the preferred 40% duty cycle, the ON-time of each diode will be 96 counts long. Further, a separate starting count for each LED will be required. It will thus be understood that each block of memory will contain at least information indicating the count corresponding to the start of the ON-time for each of the separate LEDs 301-324.

The value of the starting count of the microprocessor clock for each of the LEDs will be output on the data bus 510. The microprocessor 500 will add 96 to the value of the starting count to determine the value of the stop count. Thereafter the clock count will be compared with these values. The result will be output to the LED register 512. This command register will reflect whether a discrete LED is to be in the ON or OFF state.

LED register 512 will receive from the microprocessor 500 in a bit-mapped form. Each bit in the register will address an discrete LED. One bit in this register will be a gate enable signal for the LED gates. When this bit is set, LED illumination information will be gated from LED register 512, by LED gates 518, to LED drivers 515. There is a LED driver for each discrete LED. Each driver furnishes the power to illuminate its associated LED when the corresponding bit in the LED register is set and the LED gates are enabled.

In use, and for each scan of a selected prescription to be scanned, the LED register will be loaded with ON or OFF data for each of the LEDs. Assuming the preferred complete cycle of 240 counts, each scan at a particular prescription will consume at least a full 240 counts. Scan will occur on a block by block basis through the look up table 502 at portion 506.

Having set forth the cycling of the individual LEDs, the simpler case of the cycling of the detectors can now be set forth.

For the cycling of the detectors, sequencers 520 and 521 will be utilized. Sequence 520 will cycle detectors 41-45 (see FIG. 2A) for detection in the X direction. Sequencer 521 will cycle detectors 41-45 for detection in the Y direction.

Each of the sequencers 520 and 521 will be selected on an alternate basis by the multiplexer 529 under control of the microprocessor 500. For sweep of Sx and for Cx related to displacement in the X direction, sequencer 520 will command the sequence of interrogation. For sweep of Sy and for Cx relating to displacement in the Y direction, sequencer 521 will command the sequence of interrogation. Control will occur through clock signal at line 525 and be initialized by a reset 526.

As set forth in FIG. 8, the cumulative output of the detectors will be utilized. Specifically, the detector array will output through an analog to digital converter 531. An output for each value swept from the table 502 will occur.

Once sweeping of a portion of look up table 502—say a portion 506 occurs, the values of signal output from the detectors 41-45 are compared for each prescription value swept. As the reader will undoubtedly recognize, the peak illustrated in FIG. 15A can be easily identified and recorded to appropriate memory.

This process will be repeated for each portion of the memory 502 in the order 507, 508 and 509. Respective maxima for each of the values swept will be recorded.

The sequence of the microprocessor interrogation and computation has been previously set forth. It will be repeated only in summary format herein.

Specifically, Sx will be swept and the maximum recorded. Thereafter Sy will be swept and its maxima recorded. The two values Sx and Sy will most likely occur at differing values. The difference between these values will directly relate to cylinder C+. From C+, the actual values of sphere S can be computed using the relationship of equations [3] and [4].

Thereafter, as assuming a value for sphere S and C+, cross cylinder Cx will be swept. This cross cylinder will first be swept as it relates to X displacement and second will be swept as it relates to Y displacement. From these two sweeps, a value of Cx will be determined.

At this juncture, the reader will understand that tentative values for S, C+ and Cx will be present. Naturally, by assuming these values and iterating the process through sweeps reduced in scope based to the determined values, more accurate prescriptive data can be generated.

What is claimed is:

1. An optical instrument for objectively refracting the eye on the eye fundus, said instrument comprising:
   an interrogating pattern of elements configured for projection to the eye fundus;
   a reference pattern of elements configured for projection to the eye fundus for overlying said interrogating pattern for determining displacement of said interrogating pattern with respect to said reference pattern;
   one of said patterns including a first array of elements including at least five distinct and repeating elements, said elements distinct in being distinguishable one from another, said elements being repeating in that the same distinguishable element appears more than once in each said array;
   the other of said patterns including a second array of elements including at least two repeating elements, said elements being repeating in that the same element appears more than once in each said array;
   optics for relaying respective images of said interrogating pattern along a first optical path through the lens of said eye and onto said eye fundus and relaying the respective images of said reference pattern along a second optical path through a different portion of the lens of said eye and onto the fundus of said eye;
   at least one light source for illuminating one of said respective first or second arrays for projection as said interrogating pattern onto fundus of the eye and at least two photosensitive elements optically communicated to the other of said respective second or first patterns for reading light as said reference pattern from the fundus of said eye; and, means for detecting the signal at said photosensitive elements to determine the relative displacement of said patterns on the fundus of the eye.

2. The invention of claim 1 and wherein said photosensitive elements are five in number and communicated directly to at least five distinct and repeating elements.

3. The invention of claim 1 and including means for synchronously switching said photosensitive elements.

4. The invention of claim 1 and including a light source having a plurality of light emitting diodes for illuminating one of said patterns on said eye, said light emitting diodes arrayed for projection at spaced apart locations across the lens of said eye.

5. The invention of claim 4 and wherein said light emitting diodes are temporally phased to produce at said detector an additive signal.

6. The invention of claim 1 and wherein said first array of elements includes at least five distinct and repeating elements of square area with each distinct element bordered on every side by differently distinct elements and said second array includes at least first and second rectangles, said rectangles having an area equal to 5/2nds of the area of the squares of said first array and having a length equal to twice the width elongate dimension of said first rectangle at 90° to the elongate dimension of said second rectangle.

7. The invention of claim 1 and wherein said optics pupil respective images of said interrogating pattern and said reference pattern at said eye lens with said interrogating pattern being projected through at least three points on said eye lens and said reference pattern being projected through one point on said eye lens.

8. The invention of claim 1 and including means for providing a keratometry target projected adjacent said eye, said keratometry target positioned for reflection from a cornea of said eye along the center optical path of said instrument; and means for measuring the dimension of said keratometry target attached to said instrument whereby at least the curvature in sphere, cylinder and axis of said eye may be measured.

9. The invention of claim 1 and including the prism array, said prism array disposed in the array of one of said pattern of elements.

10. The optical instrument of claim 1 and wherein: said photosensitive elements include a charge coupled device.

11. A process for objectively refracting the eye, said process comprising:

providing an interrogating pattern of elements configured for projection to the eye;

providing a reference pattern of elements configured for projection to the eye, said reference pattern for overlying said interrogating pattern for determining the displacement of said interrogating pattern with respect to said reference pattern;

providing to said respective patterns a first array of at least five distinct and repeating elements, said elements distinct in being distinguishable one from another, said elements repeating in that the same distinguishable element appears more than once in said array;

providing to said respective patterns a second array having at least two repeating elements, said elements repeating in that the same element appears more than once in said pattern;

providing relay optics for relaying respective images of said interrogating pattern and said reference pattern to and from the eye;

projecting said interrogating and reference patterns to the eye through said relay optics;

providing a light source;

illuminating said interrogating patterns with said light source along a path for projection of either said respective first or second arrays through said optics to the eye and onto the fundus of the eye;

providing photosensitive elements, projecting said reference pattern with said photosensitive elements optically communicated to the other of said respective second or first arrays along a path for projection through said optics from the eye and onto said photosensitive elements; and, measuring the difference of signal between said respective photosensitive elements to determine the relative displacement of said interrogating pattern relative to said reference pattern whereby varying displacements of said image on the fundus of said eye may be measured for determining the prescription of the eye.

12. The invention of claim 11 and wherein said provided photosensitive elements are provided synchronous switches; and switching said provided synchronous switches between positive polarity and negative polarity for detecting the presence and absence of light.

13. The process of claim 11 and wherein said provided light source includes a plurality of light emitting diodes, said diodes having a duty cycle in the range of 20% to 50%.

14. The process of claim 13 and including the step of varying the duty cycle of said diodes temporally one with respect to another to provide at said detectors additive signals.

15. The process of claim 11 and wherein the first of said provided arrays includes five distinctly different elements, each said element being square in shape and having an infinitely stackable array wherein each one of said distinct elements is surrounded by differing ones of said distinct elements on said four sides of said square and providing to said other array first and second rectangles, the major axis of said first rectangle aligned at 90° to the major axis of said second rectangles.

16. The process of claim 11 and including the step of projecting said reference or interrogating pattern through at least at one point on the eye lens, and projecting said interrogating or reference pattern through at least three points on said eye lens, pupiled at each point of incidence on said eye lens.

17. The process of claim 11 and including providing a keratometry target surrounding said eye; and projecting an image of said keratometry target to means for measuring the dimension of said keratometry target whereby the curvature of said eye may be detected.

18. The process of claim 11 and wherein the step of providing a light source includes the step of providing an array of light emitting diodes, said provided array of light emitting diodes for projecting through an area exceeding the dimension of the iris of said eye whereby vignetting of said light emitting diodes by the iris of said eye indicates the dimension of said iris of said eye.

19. The process of claim 11 and wherein said step of providing a light source includes the step of providing a plurality of light sources selected to overlie a preselected portion of the optic being examined, said preselected portion being less than the total expanse of said optic.

20. The process of claim 11 and wherein said providing photosensitive elements step includes the step of:
providing a charge coupled device.

21. A process for objectively refracting the eye through projection optics, said process comprising the steps of:
providing an interrogating pattern of elements for projection to the eye;
providing a reference pattern of elements configured for projection to the eye for overlying said interrogating pattern to determine displacement of said interrogating pattern with respect to said reference pattern;
projecting both said patterns to the eye with a pupil of said projected patterns passing through the lens of said eye at distinctly different points;
providing to one of said patterns an array of five distinct and repeating elements, said elements being distinct in being distinguishable one from another, said elements repeating in that the same distinguishable element appears more than once in each pattern;
providing to the other of said patterns an array of at least two repeating elements, said elements repeating in that the same element appears more than once in each said pattern;
providing a plurality of light sources;
providing a plurality of photosensitive elements;
illuminating said respective first or second array by said plurality of light sources;
optically communicating said respective second or first array to said photosensitive elements; and,
timing the duty cycle of said light emitting sources to provide at said photodetectors an additive signal upon displacement of said patterns on the fundus of said eye.

22. The invention of claim 21 and including dividing said light emitting sources into first and second groups;
shifting the temporal illumination of said first group by 90° in a first and positive direction; and,
shifting the temporal illumination of said phase of the remaining half of said light sources in the opposite direction;
measuring the sensitivity at said detectors to determine the magnitude and sense of the resultant received signal.

23. The process of claim 21 and including the step of utilizing five photosensitive elements to said five distinct and repeating elements of said first pattern;
illuminating light sources on a 40% duty cycle said distinct and repeating elements of said second pattern.

24. The process of claim 21 and including successively advancing and retarding alternate duty cycle duration on each said light source.

25. The process of claim 24 and wherein said advance and said retard of said duty cycle moves advancing said duty cycle by 5% and retarding said cycle by 5% in sequential illumination of each said light source.

26. The process of claim 21 and wherein said providing photosensitive elements step includes the step of:
providing a charge coupled device.

27. A process for objective refracting a human eye, said process comprising the steps of:
providing an interrogating pattern of elements configured for projection through said eye;
providing a reference pattern of elements configured for projection overlying said interrogating pattern through said eye, said projection pattern and said interrogating pattern having relative sensitivity one to another upon relative displacement one to another;
providing one of said patterns with a first array of elements with at least five distinct and repeating elements, said elements distinct in being distinguishable from one another, said elements repeating in that the same element appears more than once in each pattern;
providing the other of said patterns with a second array of elements of at least two repeating elements, said elements repeating in that the same element appears more than once in each said array;
projecting a plurality of light sources through one said array through said eye to pupil said sources at said eye and to project said resultant pattern beyond said eye to an imaging surface on the regina;
projecting a second of said arrays to photosensitive elements, each element of said array communicated to one of said photosensitive elements;
interrogating said eye with an estimated prescription including a component of corrective cylindrical lens power provided by providing differing timing to differing ones of said plurality of light sources;
shifting the phase f half said light sources on one side of said array of said light sources 90° in duty cycle in a first temporal direction;
shifting the phase of the other half of said light sources in said array of said light sources in duty cycle 90° in the opposite temporal direction;
receiving at said photosensor said shifted phase to determine the sense and magnitude of optical change required for said estimated corrective prescription in an iterative procedure.

28. The process of claim 27 and including the step of sequencing the detectors in a first sequence to sensitize said detectors to displacement along a first axis across the imaging surface; and
sequencing said detectors to a second sequence, said second sequence for sensitizing said detectors for displacement of said pattern along and towards a direction normal to said first axis across said imaging surface.

29. The process of claim 27 and wherein said projecting the second of said arrays to photosensitive elements includes the step of projecting the second of said arrays to charge coupled devices.

* * * * *